United States Patent [19]

Anderson, Jr. et al.

[11] Patent Number: 4,863,911

[45] Date of Patent: Sep. 5, 1989

[54] METHOD FOR TREATING MALE SEXUAL DYSFUNCTION

[75] Inventors: Wesley R. Anderson, Jr.; Nicholas S. Bodor; James W. Simpkins, all of Gainesville, Fla.

[73] Assignee: University of Florida, Gainesville, Fla.

[21] Appl. No.: 892,861

[22] Filed: Aug. 4, 1986

[51] Int. Cl.$^4$ .............................................. A61K 31/58
[52] U.S. Cl. .................................................... 514/176
[58] Field of Search ......................................... 514/176

[56] References Cited

U.S. PATENT DOCUMENTS

| | | | |
|---|---|---|---|
| 4,035,507 | 7/1977 | Bodor et al. | 514/538 |
| 4,479,932 | 10/1984 | Bodor et al. | 424/9 |
| 4,521,421 | 6/1985 | Foreman | 544/250 |
| 4,540,564 | 9/1985 | Bodor et al. | 514/176 |
| 4,617,298 | 10/1986 | Bodor et al. | 514/909 |

OTHER PUBLICATIONS

Malmnas, *Acta Physiologica Scand.* (Suppl. 395): 9–46, 1973.
Damassa et al., *Hormones and Behavior* 8: 275–286, 1977.
Davidson et al., in S. Levine (Ed.), *Hormones and Behavior*, Academic Press, New York, 1972, pp. 63–103.
MacLusky et al., in *Metabolism of Hormonal Steroids in the Neuroendocrine Structures*, eds. F. Celotti et al., Raven Press, vol. 13, 1984, pp. 103–116.
McEwen, *Science* 211: 1303–1311, 1981.
Beyer et al., *Hormones and Behavior* 7: 353–363, 1976.
Bonsall et al., *Life Sciences* 33: 655–663, 1983.
Michael et al., *Endocrinology* 118: 1935–1944, 1986.
Krey et al., *Brain Res.* 193: 277–283, 1980.
Pfaff, *J. Comp. Physiol. Psych* 73: 349–358, 1970.
Sodersten, *Hormones and Behavior* 4: 247–256, 1973.
Gray et al., *Physiology and Behavior* 24: 463–468, 1980.
Christensen et al., *Endocrinology* 95: 984–990, 1974.
Lisk et al., *Neuroendocrinology* 36: 211–217, 1983.
Baum et al., *Science* 182: 283–285, 1973.
Larsson et al., *Hormones and Behavior* 4: 289–299, 1973.
DeBold et al., *Hormones and Behavior* 11: 401–413, 1978.
Katzenellenbogen, Chem. Abst. vol. 101, 48830b (1984).
Bodor, Chem. Abst. 97-6651n (1982).

*Primary Examiner*—Cecilia Shen
*Attorney, Agent, or Firm*—Mary Katherine Baumeister; Dennis P. Clarke

[57] ABSTRACT

The invention provides a method for treating sexual dysfunction in male mammals using a compound of the formula

[E—DHC]                (I)

or a non-toxic pharmaceutically acceptable salt thereof, wherein [E] is an estrogen and [DHC] is the reduced, biooxidizable, blood-brain barrier-penetrating, lipoidal form of a dihydropridine⇌pyridinium salt redox carrier. Compositions for use in the subject method are also disclosed. A preferred compound for use in the method and compositions is an estradiol derivative, namely, 17β-[(1-methyl-1,4-dihydro-3-pyridinyl)carbonyloxy]estra-1,3,5(10)-trien-3-ol.

25 Claims, 7 Drawing Sheets

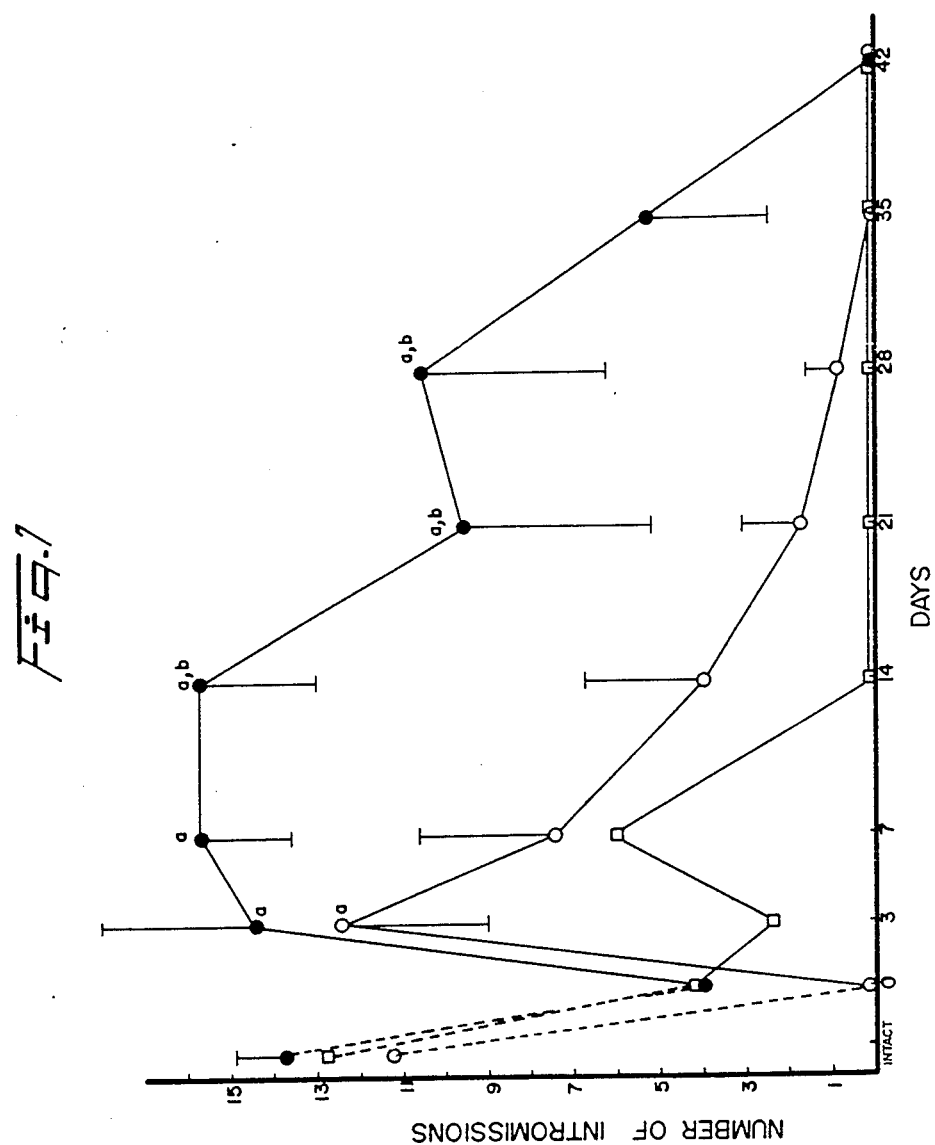

METHOD FOR TREATING MALE SEXUAL DYSFUNCTION

FIELD OF THE INVENTION

The present invention relates to the use of brain-specific dihydropyridine redox carrier-type derivatives of estrogenic agents for treating sexual dysfunction in male mammals.

BACKGROUND OF THE INVENTION

Male sexual behavior is composed of proceptive and consummatory behaviors. The proceptive behaviors include the awareness of the presence of a receptive female, the pursuit of that female and the positioning of the body (mounting) to allow insertion of the penis into the vagina. This latter behavior, termed intromission, as well as its prerequisite erection of the penis and eventual ejaculation, are the consummatory components of masculine sexual behavior. The accomplishment of ejaculation requires the entire repertoire of the aforementioned behaviors. It is dependent upon the close coordination of sensory and motor components of the nervous system which are coordinated at the levels of the brain and by spinal reflexes.

Male sexual behavior is steroid-dependent and in most mammals testosterone, released by the Leydig cells of the testes, is the hormone involved in permitting the expression of masculine behavior. In sexually experienced male rats, castration results in a gradual diminution and an eventual extinction of masculine sexual behavior. Replacement of the hormone testosterone completely prevents the loss of masculine sexual behavior [Malmnas, Acta Physiologica Scand. (Suppl. 395): 9–46, 1973; Damassa et al, Hormones and Behavior 8: 275–286, 1977]. Additionally, if after castration masculine sexual behavior is allowed to wane prior to the initiation of testosterone replacement, testosterone replacement can restore the full expression of the behavior [Davidson et al, in S. Levine (Ed.) Hormones and Behavior, Academic Press, New York, 1972, pp. 63–103].

Three lines of evidence indicate that the proceptive components of masculine sexual behavior are dependent upon the aromatization in the brain of testosterone to estradiol. First, it has now been conclusively demonstrated that the blockade of the conversion of testosterone to estradiol with aromatase inhibitors or the blockade of estrogen actions with antiestrogens antagonize the effects of testosterone on masculine sexual behavior. Consistent with this notion of testosterone metabolism into estradiol which activates masculine sexual behavior is the distribution of the enzyme, aromatase. In mammals, aromatase is reported to be concentrated in the preoptic area, the hypothalamus, and the amygdala brain regions known to mediate the effects of testosterone on masculine sexual behavior. For representative literature, see: N. J. MacLusky, A. Philip, C. Hurlburt and F. Naftolin, in Metabolism of Hormonal Steroids in the Neuroendocrine Structures, Eds. F. Celotti, F. Naftolin and L. Martini, Raven Press, Vol. 13, 1984, pp. 103—116; B. S. McEwen, Science 211: 1303—1311, 1981; Beyer et al, Hormones and Behavior 7: 353–363, 1976.

Second, following the systemic administration of testosterone, estradiol appears as the major androgen metabolite in regions of the brain known to mediate masculine sexual behavior. In one study of Rhesus monkeys, [$^3$H]-testosterone was administered systemically and sections of the brain were extracted to determine the steroid metabolites present. In the hypothalamus, preoptic area and amygdala, 50% or more of the radioactivity was reported to be estradiol, while in other brain structures, the radioactivity remained as testosterone. In contrast, in peripheral tissues such as the seminal vesicles, glans penis and the prostate gland, dihydrotestosterone was the major metabolite (R. W. Bonsall et al, Life Sciences 33: 655–663, 1983). In a subsequent study, which more extensively evaluated testosterone metabolism in brain regions, only the hypothalamus, preoptic area and amygdala were found to form estradiol significantly (61, 43 and 64%, respectively). All other brain areas evaluated contained either no estradiol or less than 10% of the recovered steroids (R. P. Michael et al, Endocrinology 118: 1935–1944, 1986). Finally, the amount of estradiol bound to nuclear receptors in the preoptic area-hypothalamus is directly related to the level of testosterone in the serum, suggesting that the source of estradiol bound to its receptor in this brain region is circulating testosterone (L. C. Krey et al, Brain Res. 193: 277–283, 1980).

Third, estradiol stimulates the proceptive components of masculine sexual behavior. Pfaff (J. Comp. Physiol. Psych. 73: 349–358, 1970) administered estradiol benzoate systemically (10 µg/day) for 9 to 11 days to castrated male rats and observed that estradiol increased mounting, intromissions and ano-genital sniffing and reduced mounting latency to levels comparable to that observed following the administration of testosterone propionate (200 µg/day). Sodersten (Hormones and Behavior 4: 247–256, 1973) administered estradiol benzoate (100 µg/day) for 24 to 28 days to male rats castrated 6 weeks previously and found that mounts and intromissions were equivalent to those observed following similar treatment with testosterone propionate (100 µg/day). Ejaculations were less affected by estradiol benzoate then by testosterone propionate. Gray et al (Physiology and Behavior 24: 463–468, 1980) administered Silastic pellets containing estradiol and evaluated sexual behavior 7 days later. They observed that estradiol stimulated mounting behavior but was less effective than testosterone in enhancing intromissions and ejaculations.

Two studies have evaluated the effects of estradiol implanted into the brain on masculine sexual behavior. In one study, castrated rats were implanted bilaterally with cannulae into the preoptic area and 10 µg of estradiol was delivered through each cannulae every 3 days for 12 days. Estradiol was reported to be more effective than testosterone in inducing mounts and intromissions (Christensen and Clemens, Endocrinology 95: 984–990, 1974). Lisk and Greenwald (Neuroendocrinology 36: 211–217, 1983) reported that preoptic area implantation of estradiol benzoate (no dosage indicated, 23 gauge cannulae used) stimulated mounting, but not intromissions, to levels observed in normal male golden hamsters. While it appears that estradiol acts centrally to stimulate masculine sexual behavior, the two aforementioned studies utilized high drug doses which could readily diffuse out of the brain. Thus, it is not certain from these reports to what extent a central versus peripheral action of estradiol is related to the stimulation of masculine sexual behavior.

Estradiol does not fully restore masculine sexual behavior in castrated male rats. Rather, it stimulates the proceptive components of the behavior. Thus, it is not surprising that in most studies, administration of estradiol alone had less effect on ejaculatory behavior than on mounting and intromission behavior in rats. For representative literature, see: Baum and Vreeburg, Science 182: 283-285, 1973; Christensen and Clemens, Endocrinology 95: 984-990, 1974; Gray et al, Physiology and Behavior 24: 463-468, 1980; Larsson, Sodersten and Beyer, Hormones and Behavior 4: 289-299, 1973; Lisk and Greenwald, Neuroendocrinology 36: 211-217, 1983; Sodersten, Hormones and Behavior 4: 247-256, 1973.

To test the hypothesis that central stimulation by estradiol and peripheral stimulation by dihydrotestosterone were the mechanisms by which testosterone stimulates masculine sexual behavior, several studies have utilized both estradiol and dihydrotestosterone in combination. Larsson et al (Hormones and Behavior 4: 289-299, 1973) reported that, while dihydrotestosterone-treatment of castrated male rats was ineffective alone, in combination with estradiol benzoate it returned each component of masculine sexual behavior to levels observed in normal male rats. DeBold and Clemens (Hormones and Behavior 11: 401-413, 1978) reported that, in castrated male rats, treatment with estradiol benzoate plus dihydrotestosterone induced the complete male sexual behavior pattern, while either hormone alone was much less effective. Finally, Lisk and Greenwald (Neuroendocrinology 36: 211-217, 1983) reported that, while preoptic area implants of estradiol benzoate had little effect on intromission behavior in castrated male rats, the combination of estradiol benzoate (into the preoptic area) and systemic treatment with dihydrotestosterone returned intromission behavior to levels observed in normal intact male rats. They concluded that the combination of central stimulation by estradiol and peripheral stimulation by dihydrotesterone reinstated a behavior equivalent to that stimulated by testosterone.

While it would appear from the available literature that estradiol acts in the brain to stimulate masculine sexual behavior, these data must be considered with some caution. That is, every study which has evaluated estradiol effects on sexual behavior has used routes of administration which deliver the hormone to both the central nervous system and the periphery. Even implants of estradiol into the brain result in a rapid delivery of the hormone to the periphery. Thus, the relative contribution of central versus peripheral effects of estradiol on masculine sexual behavior has not been demonstrated with certainty.

At the present time, estrogens are not used to treat male sexual dysfunctions, primarily because of significant undesirable side-effects. Estrogens are, however, generally administered to control symptoms of menopause; for postmenopausal osteoporosis, dysmenorrhea, menorrhagia, amenorrhea, atrophic vaginitis, ovarian dwarfism and post-partum breast engorgement; in combination with progestins in oral contraceptives; in breast cancer; and in men in prostatic carcinoma. These uses are a reflection of the significant physiological and pharmacological actions of the estrogens, especially on the reproductive organs. Unfortunately, some significant toxic effects, including increased risk of thromboembolism, thrombophlebitis and endometrial carcinoma, are associated with the use of these hormones in therapy. Additionally, in the male, estrogen treatment stimulates gynecomastia, causes testicular regression and feminizes hair growth patterns.

Recently, a chemical delivery system (CDS) has been devised which promises to deliver centrally acting drugs, such as the estrogens, to the brain in a sustained and site-specific manner. In accord with this system, the desired centrally-mediated hormonal effects of the estrogens can be achieved without the high concentrations throughout the body which are believed to be responsible for the significant toxic effects generally associated with use of these drugs. The estrogen-chemical delivery system is generally described in Bodor U.S. Pat. No. 4,479,932 issued to UNIVERSITY OF FLORIDA on Oct. 30, 1984, and more specifically in UNIVERSITY OF FLORIDA's International Application No. PCT/US83/00725 (published under International Publication No. WO83/03968), in Bodor U.S. Pat. No. 4,540,564 issued to UNIVERSITY OF FLORIDA on Sept. 10, 1985, and in copending Bodor U.S. patent application Ser. Nos. 665,940 and 666,210, both filed Oct. 29, 1984. Briefly, according to the estrogen-CDS system, the target estrogen is tethered to a reduced, blood-brain barrier-penetrating lipoidal form of a dihydropyridine⇌pyridinium salt type redox carrier. Oxidation of the dihydropyridine carrier moiety in vivo to the ionic pyridinium salt type estrogen/carrier entity prevents elimination thereof from the brain, while elimination from the general circulation is accelerated, and subsequent cleavage of the quaternary carrier/estrogen species results in sustained delivery of the estrogen in the brain and facile elimination of the carrier moiety. As stated in the aforementioned U.S. Pat. No. 4,479,932, the rationale for brain delivery of the steroid hormones, e.g. estradiol, at least in part derives from the fact that recent studies of histological mapping of hormone-sensitive and specific steroid-binding cells in the brain have underscored the importance of steroid action in the brain on sexual behavior. Further details of the estrogen-chemical delivery system are given hereinbelow.

More recently, it has been found that the redox carrier-estrogen derivatives described in the aforementioned patents are useful in achieving weight control in mammals; cf. Bodor et al copending U.S. patent application Ser. No. 790,159, filed Oct. 22, 1985, now U.S. Pat. No. 4,617,298. Related literature on the carrier-estrogens reports sustained LH inhibition and sustained reduction of body weight increases (Estes et al, Program, 67th Annual Meeting of the Endocrine Society, Baltimore, MD, p. 52, 1985; Estes et al, 68th Annual Meeting of the Endocrine Society, Anaheim, CA, p. 288, 1986).

SUMMARY AND OBJECTS OF THE INVENTION

One object of the present invention is to provide a new method for treating male sexual dysfunction, including psychological impotence, particularly in human beings and in domestic animals, zoo animals and rare or endangered mammalian species.

Another object of the present invention is to provide pharmaceutical compositions for use in the treatment of male sexual dysfunction.

Yet another object of this invention is to provide a new use for brain-specific dihydropyridine redox carrier type derivatives of estrogenic agents in improving sexual function in male mammals.

Still another object of this invention is to provide long-acting compositions containing brain-specific dihydropyridine redox carrier-type derivatives of estrogenic agents for use in improving male sexual desire.

Another object of the present invention is to provide novel means for raising libido in a male mammal in need of same.

In accord with the foregoing objects of the invention, there is described herein a novel method for improving sexual function in a male mammal, said method comprising administering to a male mammal in need of such treatment, an amount effective to improve sexual function in said male mammal of a compound of the formula $$[E-DHC] \qquad (I)$$

or a non-toxic pharmaceutically acceptable salt thereof, wherein [E] is an estrogen and [DHC] is the reduced, biooxidizable, blood-brain barrier-penetrating lipoidal form of a dihydropyridine⇌pyridinium salt redox carrier.

BRIEF DESCRIPTION OF THE DRAWINGS

Other objects and advantages of the present invention will be apparent from the following detailed description and accompanying drawings, in which:

FIG. 7 is plot of mean intromission frequency, per minute, versus time, in days, following a single i.v. injection of $E_2$-CDS ( ● ), $E_2$-VAL ( ○ ) or DMSO (□) to castrated male rats.

DETAILED DESCRIPTION OF THE INVENTION

Figure 1:
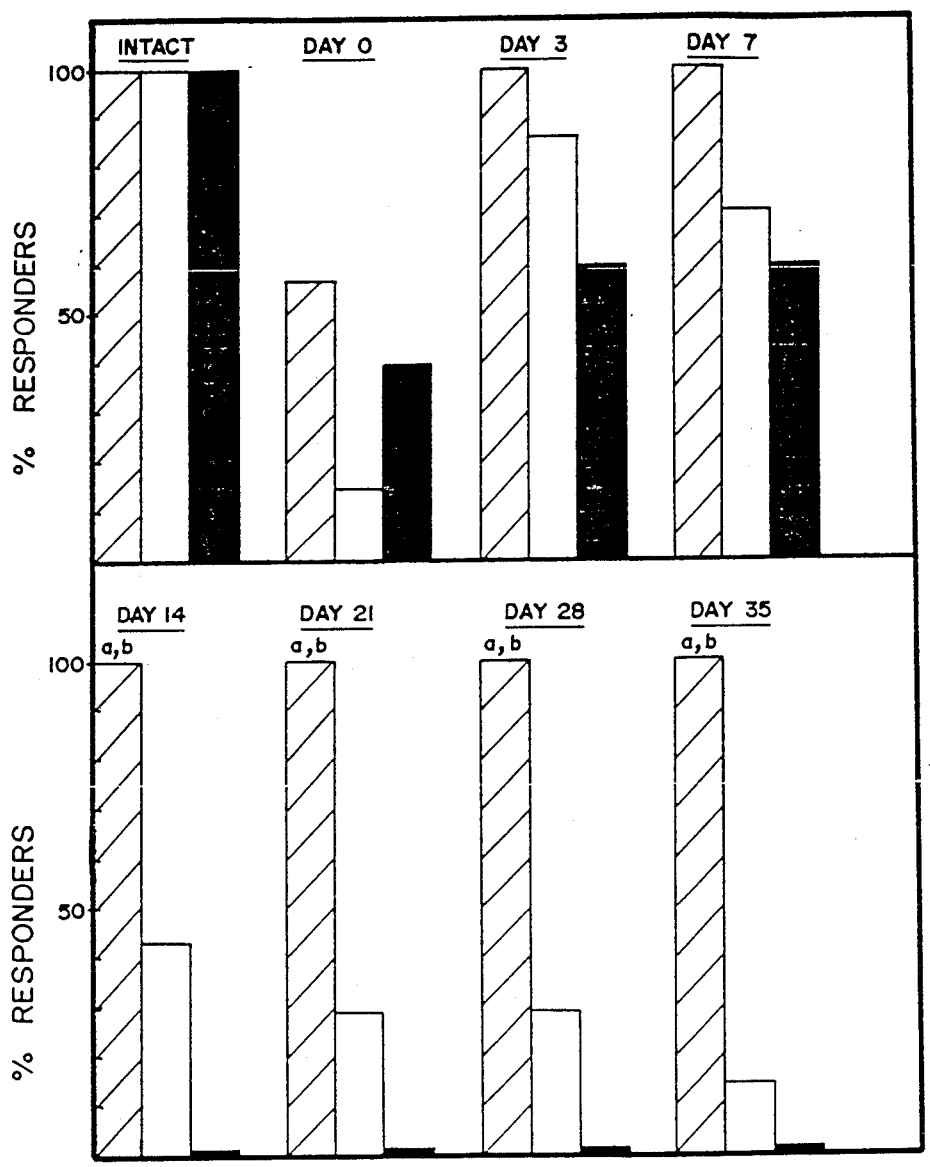
FIG. 1 is a bar graph illustrating the effects of a representative estradiol-CDS, i.e. 17β-[(1-methyl-1,4-dihydro-3-pyridinyl)carbonyloxy]estra-1,3,5(10)-trien-3-ol, hereafter referred to as $E_2$-CDS ( ▨ ), of estradiol valerate, hereafter referred to as $E_2$-VAL (□), and of dimethylsulfoxide vehicle, hereafter referred to as DMSO ( ■ ), on the mounting percentage (percent responders) in castrated male rats from day 0 to day 35 after a single intravenous (i.v.) injection.

The term "estrogen", e.g. as used in connection with formula (I), is employed herein in its conventional sense and thus comprises the natural estrogens, the semi-synthetic estrogens and the synthetic estrogens. See, for example, Cutting's Handbook of Pharmacology, seventh edition, ed. T. Z. Csáky, M.D. and Byron A. Barnes, Ph.D., Appleton-Century-Crofts, Norwalk, Conn., 1984, Part 14, Chapter 35, pp. 427–432.

Preferred compounds for use in the method and compositions of this invention can be represented by the formula $$E-DHC]_n \qquad (Ia)$$

wherein E— is the residue of an estrogen containing at least one reactive hydroxyl functional group, said residue being characterized by the absence of a hydrogen atom from at least one of said reactive functional groups in said estrogen; n is a positive integer equal to the number of said functional groups from which a hydrogen atom is absent; and [DHC] is the reduced, biooxidizable, blood-brain barrier-penetrating, lipoidal form of a dihydropyridine⇌pyridinium salt redox carrier. In formula (Ia), n is preferably 1, 2 or 3, more preferably 1 or 2 and most preferably 1.

Among the estrogens whose derivatives of formulas (I) and (Ia) are intended for use in the method and compositions of this invention, there can be mentioned natural estrogens, i.e. estradiol and its 3- or 17-monoesters such as estradiol benzoate, estradiol cypionate, estradiol enanthate, estradiol undecylate, estradiol valerate, estradiol propionate and estradiol undecenylate, as well as estrone and estriol; semisynthetic estrogens, for example ethinyl estradiol, mestranol, quinestrol, estrazinol, estrofurate and nylestriol; and synthetic estrogens; e.g. benzestrol, diethylstilbestrol, dienestrol and hexestrol. Preferably, the estrogenic portion of the compounds of formulas (I) and (Ia) has a steroidal structure, i.e. it is derived from a natural or semi-synthetic estrogen; more preferably, it is derived from a 3-monohydroxy, 17-monohydroxy or 3,17-dihydroxy steroid having an aromatic A-ring, a carrier moiety [DHC] replacing the monohydroxy group in the 3- or 17-monohydroxy steroid, and replacing one or both hydroxy groups in the 3,17-dihydroxy steroid. At the present time, compounds derived from estradiol by replacement of one or both hydroxyl functions with carrier groupings are most especially preferred for use in the method and compositions of this invention.

The term "lipoidal" as used herein is intended to designate a carrier moiety which is lipid-soluble or lipophilic, as in the earlier Bodor patents and applications referenced hereinabove.

The expression "non-toxic pharmaceutically acceptable salts" are used herein generally includes the non-toxic salts of the compounds of formulas (I) and (Ia) hereinabove formed with non-toxic, pharmaceutically acceptable inorganic or organic acids of the general formula HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a pharmaceutically acceptable organic or inorganic acid" as used herein, e.g. in connection with formula (II) hereinbelow, is intended to include anions of such HX acids.

It will be appreciated from the foregoing that a compound of formula (I) may be administered as the free base or in the form of a non-toxic pharmaceutically acceptable salt thereof, i.e. a salt which can be represented by the formula

[E—DHC].HX wherein the structural variables are defined as before; and that, regardless of the actual form in which the compound is administered, it will be converted in vivo to a quaternary salt of formula (II) hereinbelow, $X^-$ being present in vivo. It is not necessary that the anion be introduced as part of the compound administered. Indeed, even when the compound of formula (I) is used in its salt form, the anion of the formula (II) compound in vivo is not necessarily the same as that present in the formula (I) compound. In fact, the exact identity of the anionic portion of the compound of formula (II) is immaterial to the in vivo transformation of (I) to (II).

The compounds of formula (I) which are employed in the method and compositions of the present invention can be synthesized by methods described in the aforementioned Bodor U.S. Pat. Nos. 4,479,932 and 4,540,564, Bodor copending U.S. Ser. Nos. 665,940 and 666,210, Bodor et al copending U.S. Ser. No. 790,159 and University of Florida PCT/US83/00725 (International Publication No. WO83/03968). Synthesis generally begins with preparation of the corresponding quaternary intermediates of the formula $$[E-QC^+]X^- \tag{II}$$

wherein $X^-$ is the anion of a non-toxic pharmaceutically acceptable acid, [E] is an estrogen and [QC$^+$] is the hydrophilic, ionic pyridinium salt form of a dihydropyridine⇌pyridinium salt redox carrier. In the case of preparation of the preferred compounds of formula (Ia), the corresponding quaternary intermediates have the formula $$E-QC^+]_n qX^{-t} \tag{IIa}$$

wherein E— and n are as defined with formula (Ia); [QC$^+$] and $X^-$ are as defined with formula (II); t is the valence of the acid anion; and q is the number which when multiplied by t is equal to n. The pyridinium salts of formulas (II) and (IIa) are not only chemical intermediates to the corresponding compounds of formulas (I) and (Ia), respectively, but also represent the form of the chemical delivery system which is "locked in" the brain following administration of the dihydro derivative.

The preparation of the intermediates of formula (II) is tailored to the particular estrogen portion and carrier portion to be combined, especially to the nature of the chemical bond between them and the presence or absence of other reactive functional groups, which may need to be protected during particular stages of the synthetic pathway. In forming the intermediates of formula (I), at least one reactive functional group, for example a hydroxyl, amino, mercapto, amide or imide group, in the estrogen will be bonded to [QC$^+$], the hydrophilic, ionic pyridinium salt form of a dihydropyridine⇌pyridinium salt redox carrier.

It will be appreciated that by "dihydropyridine carrier" or "[DHC]", there is intended any non-toxic carrier moiety comprising, containing or including the dihydropyridine nucleus, whether or not a part of any larger basic nucleus, and whether substituted or unsubstituted, the only criteria therefor being capacity for penetration of the blood-brain barrier (BBB) and in vivo oxidation thereof to the corresponding quaternary pyridinium salt carrier [QC$^+$]. As aforesaid, the ionic pyridinium salt estrogen/carrier prodrug entity [E—QC$^+$] which results from such in vivo oxidation is prevented from efflux from the brain, while elimination from the general circulation is accelerated. Subsequently, the bond coupling the estrogen species to the quaternary carrier [QC$^+$] is metabolically cleaved, which results in sustained delivery of the estrogen in the brain and facile elimination of the carrier moiety [QC$^+$]. And the cleavage of the quaternary compound (II) to sustainedly deliver the estrogen in the brain with concomitant facile elimination of the carrier moiety [QC$^+$] is characteristically enzymatic cleavage, e.g., by esterase, peptidase, amidase, cholinesterase or hydrolytic enzyme, albeit any type of in brain cleavage which might result, whether enzymatic, metabolic or otherwise, of course remains within the ambit of the delivery system.

Many different dihydriopyridine⇌pyridinium salt redox carrier moieties are disclosed in the earlier Bodor patents and applications referenced hereinabove. Obviously, the choice of carrier will be at least partially dictated by the structure of the estrogen selected for derivatization. Most estrogens contain at least one free hydroxyl group which can be conveniently linked to a carrier moiety to give the intermediates of formula (IIa) and, ultimately, the compounds of formula (Ia). The following major classes of quaternaries are prime examples of the carrier moieties encompassed hereby for linkage to an estrogen having at least one hydroxyl functional grouping, replacing a hydrogen atom from at least one of said functional groupings with one of the following [QC+] groupings:

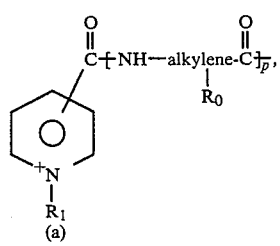
(a)

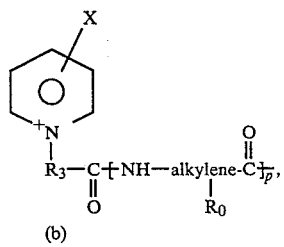
(b)

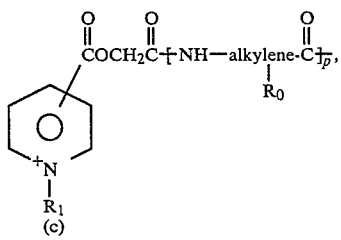
(c)

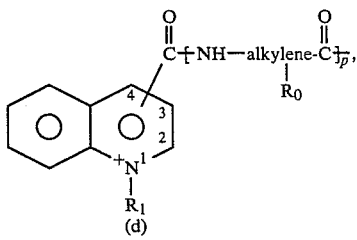
(d)

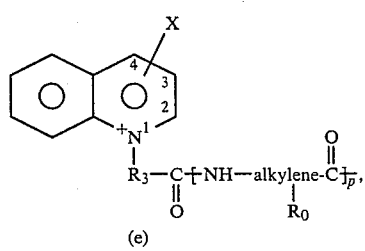
(e)

-continued

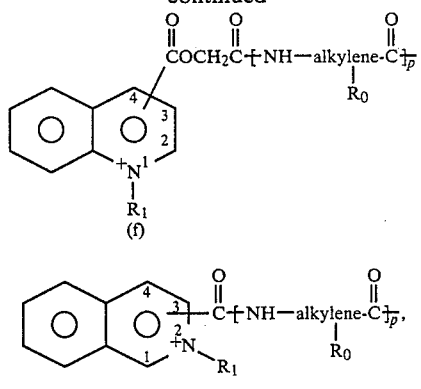
(f)

(g)

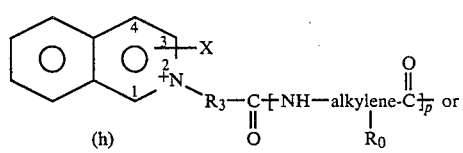
(h)

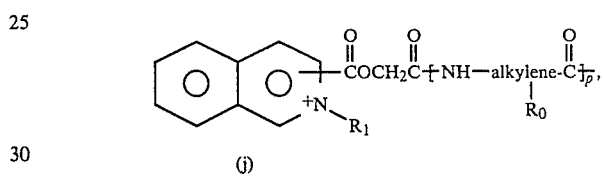
(j)

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring.

Here and throughout this application, the expression "$C_1$-$C_7$ haloalkyl" means $C_1$-$C_7$ alkyl substituted by one or more halogen atoms. Also here and throughout this application, the alkyl radicals, including alkyl and alkylene portions of other radicals, can be straight or branched unless otherwise specified.

The expression "$R_o$ is a radical identical to the corresponding portion of a natural amino acid" is believed to be self-explanatory. Thus, for example, $R_o$ can be hydrogen, as in glycine; methyl, as in alanine; —CH(CH$_3$)$_2$, as in valine; —CH$_2$(CH$_3$)$_2$, as in leucine;

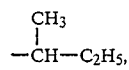

as in isoleucine;

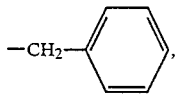

as in phenylalanine;

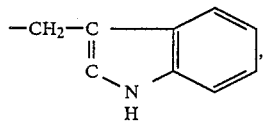

as in tryptophan; —CH₂OH, as in serine; —CH(OH)—CH₃, as in threonine; —(CH₂)₂—SCH₃, as in methionine; —CH₂—CONH₂, as in asparagine; —CH₂CH₂—CONH₂, as in glutamine;

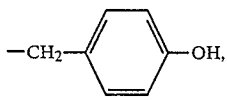

as in tyrosine; —CH₂SH, as in cysteine; —CH₂COOH, as in aspartic acid; and —CH₂CH₂COOH, as in glutamic acid. The expression "natural amino acid" as used herein does not encompass dopa or L-DOPA. Preferred amino acids encompassed by the R₀ term include glycine, alanine, valine, leucine, phenylalanine, isoleucine, methionine, asparagine and glutamine.

The dihydro forms [DHC] corresponding to the aforementioned quaternaries are as follows:

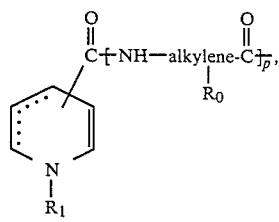 (a')

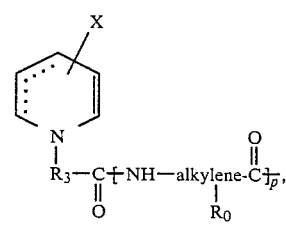 (b')

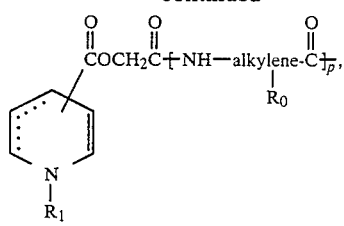 (c')

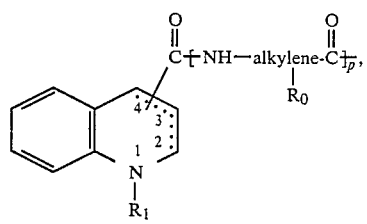 (d')

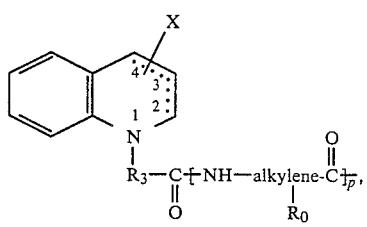 (e')

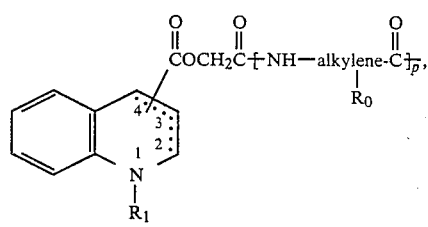 (f')

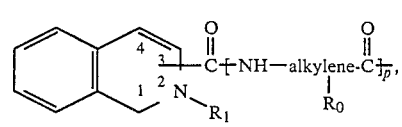 (g')

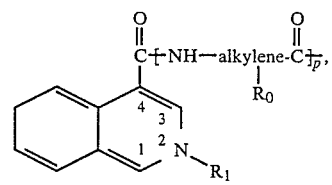 (g")

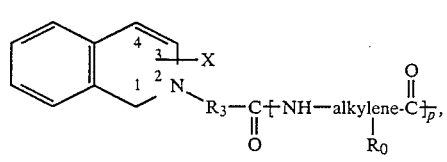 (h')

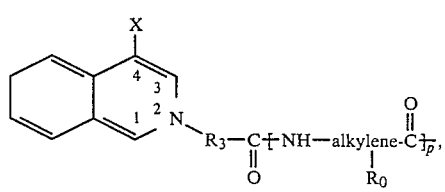 (h")

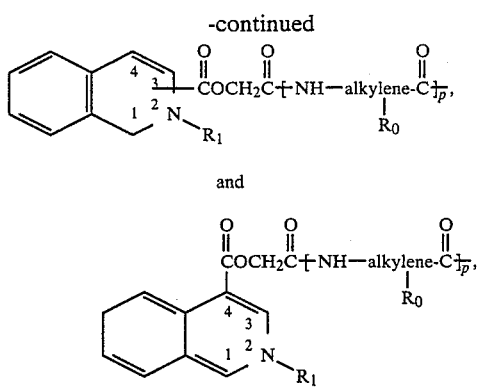

wherein the alkylene group can be straight or branched and can contain 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihuydroquinoline ring; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R" wherein R' and R", which can be the same or different, are each H or $C_1$-$C_7$ alkyl, or X is —CH=NOR'" wherein R'" is H or $C_1$-$C_7$ alkyl; the carbonyl-containing groupings in formulas (a') and (c') and the X substituent in formula (b') can each be attached at the 2, 3, or 4 position of the dihydropyridine ring; the carbonyl-containing groupings in formulas (d') and (f') and the X substituent in formula (e') can each be attached at the 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring.

The presently preferred dihydropyridine⇌pyridinium salt redox carrier moieties for use herein are those wherein p is 0 or 1, most preferably 0; alkylene, when present (i.e. p=1 or 2), is —CH$_2$—; $R_o$, when present (i.e. p=1 or 2), is H, —CH$_3$, —CH(CH$_3$)$_2$, —CH$_2$—CH(CH$_3$)$_2$,

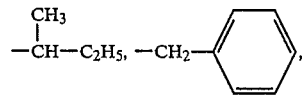

—(CH$_2$)$_2$—SCH$_3$, —CH$_2$—CONH$_2$ or —CH$_2$CH$_2$—CONH$_2$; $R_1$, when present, is —CH$_3$; $R_3$, when present, is —CH$_2$CH$_2$—; X, when present, is —CONH$_2$; the depicted carbonyl-containing groupings in formulas (a) and (c) and the X substituent in formula (b) are attached at the 3-position; the depicted carbonyl-containing groupings in formulas (d) and (f) and the X substituent in formula (e) are attached at the 3-position; and the depicted carbonyl-containing groupings in formulas (g) and (j) and the X substituent in formula (h) are attached at the 4-position; and the corresponding dihydro forms.

Especially preferred dihydropyridine⇌pyridinium salt redox carrier moieties are the quaternaries of structures (a), (b), (d), (e), (g) and (h); and the corresponding dihydro forms, most especially when they contain the preferred structural variables identified in the preceding paragraph.

Various illustrative synthetic schemes as applied to specific compounds for use herein are set forth below in the sections entitled "ILLUSTRATIVE SYNTHETIC METHODS" and "SYNTHETIC EXAMPLES". (Yet other methods are disclosed in the aforementioned earlier Bodor patents and applications.) While the sequence of reaction steps can be varied in many cases, in general the final step (except in the case of optional salt formation) will be reduction of a quaternary compound of formula (II) to the corresponding dihydro compound of formula (I). The reduction is usually conducted at a temperature from about −10° C. to room temperature, for a period of time from about 10 minutes to 2 hours, conveniently at atmospheric pressure. Typically, a large excess of reducing agent is employed, e.g. a 1:5 molar ratio of reducing agent to starting compound of formula (II). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (I) is usually insoluble in water and thus can be readily separated from the reaction medium. In the case of sodium borohydride reduction, an organic reaction medium is employed, e.g. a lower alkanol such as methanol, an aqueous alkanol or other protic solvent.

ILLUSTRATIVE SYNTHETIC METHODS

I. Methods for Derivatizing —OH Functions in Estrogens with p=0 Type Carriers

METHOD A

The estrogen is reacted with nicotinoyl chloride, with nicotinic anhydride, or with nicotinic acid in the presence of a suitable coupling agent such as dicyclohexylcarbodiimide, in an appropriate organic solvent, to afford the corresponding nicotinate. The nicotinate is then quaternized, typically by treatment with methyl iodide in a suitable organic solvent, to afford the quaternary derivative of formula (II), which is then reduced by treatment with sodium dithionite or sodium borohydride as generally described hereinabove to afford the desired compound of formula (I). When the estrogen contains more than one reactive hydroxyl function, reaction conditions may be varied so that more than one hydroxyl function will be converted to nicotinate groupings. If more than one carrier moiety is so introduced, selective hydrolysis may be employed at a later stage, e.g. after quaternization, to generate a derivative containing fewer carrier moieties, if such is desired. The representative estrogens depicted below may be derivatized in this manner to the corresponding compounds of formulas (II) and (I). 3-Monoesters and 17-monoesters of estradiol, e.g. estradiol benzoate and estradiol valerate, and estriol may be similarly derivatized, as may the other hydroxy-containing estrogens specifically mentioned in this specification.

The foregoing procedure may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this method to the corresponding picolinates and isonicotinates and then to the corresponding compounds of formulas (II) and (I).

Alternatively, the estrogen may be reacted with an activated ester of nicotinic acid, picolinic acid or isonicotinic acid, e.g. a succinimidyl ester such as

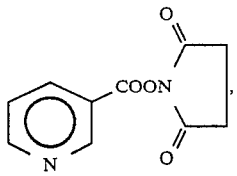

and the procedure described above repeated to afford the identical products. As yet another alternative, the activated ester, e.g. the succinimidyl ester depicted above, may be quaternized (e.g. by treatment with methyl iodide) and the quaternized activated ester then reacted with the estrogen. The quaternary compound of formula (II) thus obtained may then be reduced as described in the first paragraph of this method to give the corresponding compound of formula (I).

| STARTING MATERIAL | QUATERNARY INTERMEDIATE(CATION) | DIHYDRO DERIVATIVE |
|---|---|---|
| mestranol | | |
| estrone | | |
| quinestrol | | |

|  | STARTING MATERIAL | QUATERNARY INTERMEDIATE(CATION) | DIHYDRO DERIVATIVE |
|---|---|---|---|
| -continued | 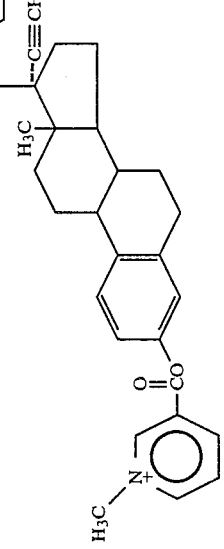ethinyl estradiol | 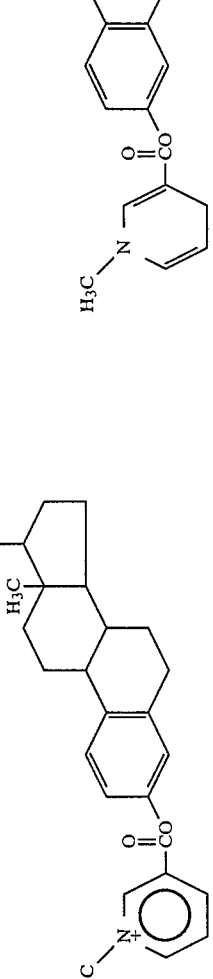 | 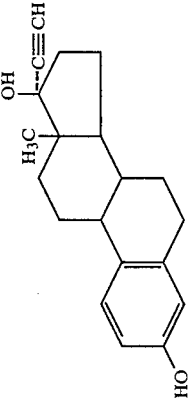 |
|  | 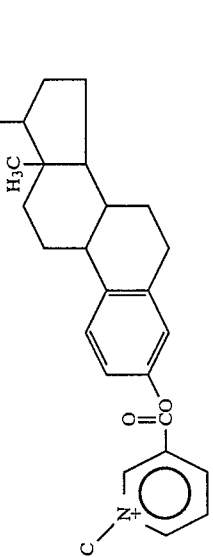estradiol |  | 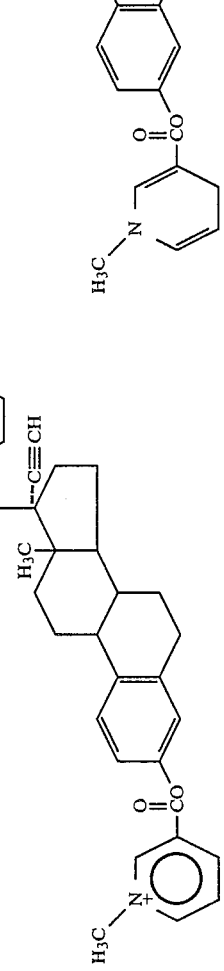 |
This compound can be selectively hydrolyzed by known methods to the corresponding 17-monoester, which can be reduced to give the preferred 17-monoester of formula (I).

| STARTING MATERIAL | QUATERNARY INTERMEDIATE (CATION) | DIHYDRO DERIVATIVE |
|---|---|---|
| benzestrol 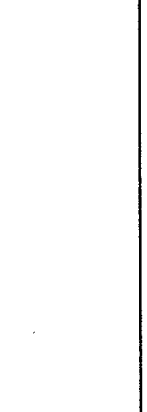 | 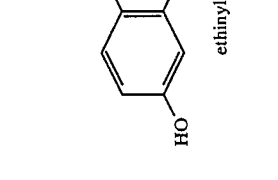 | 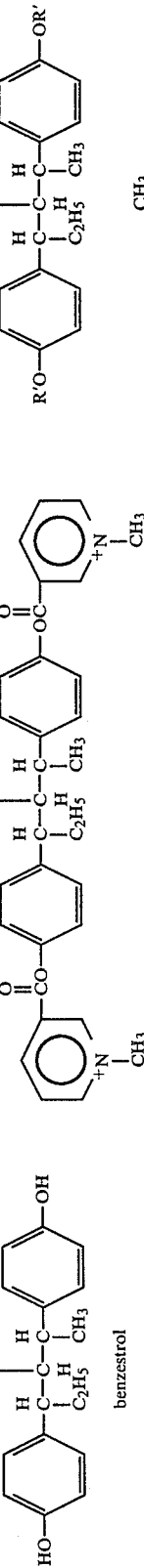 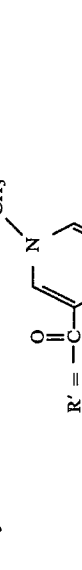 |
| ethinyl estradiol  | 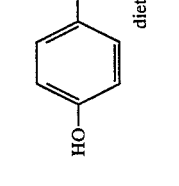 | 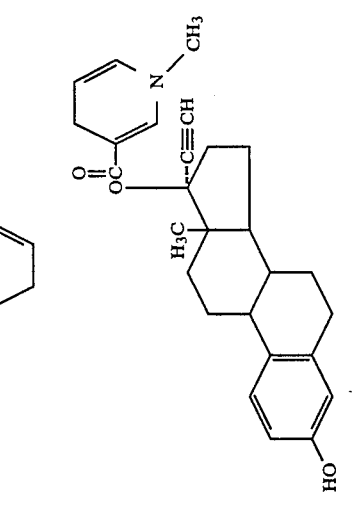 |
| diethylstilbestrol  |  | 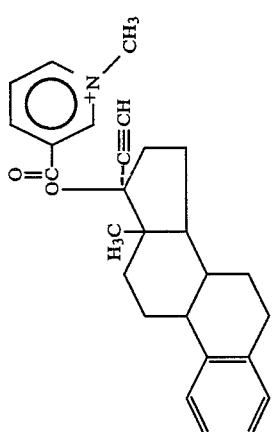 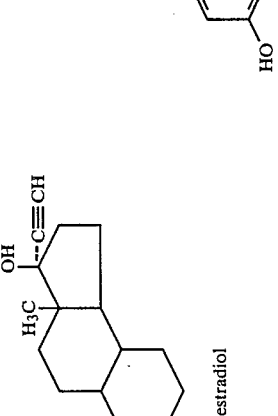 |

METHOD B

This is an alternate process for derivatizing estrogens containing secondary or tertiary hydroxyl functional groups with p=0 type carriers. According to this process, the estrogen is reacted with chloral or other aldehyde capable of forming a hemiacetal therewith. In the case of chloral, this converts the —OH function(s) to

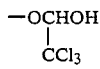

groupings. The —OH function(s) of the resultant hemiacetal can then be derivatized by any of the methods for derivatizing —OH groups disclosed herein, e.g. by reaction with nicotinic acid or its acid chloride or anhydride as described in Method A.

This process is of particular value when the —OH group(s) in the estrogen is/are sterically hindered and/or when it is desired to alter the rate of release of the estrogen from that obtained when the carrier is hooked directly to the estrogen's hydroxy function(s).

The representative estrogen depicted below may be derivatized in ths manner to the corresponding compounds of formulas (II) and (I). Other estrogens containing secondary or tertiary —OH groups which are disclosed herein, e.g. in connection with Method A, may be similarly derivatized. This method is of special interest for derivatizing steroidal estrogens containing secondary or tertiary 17β-hydroxy substituents, especially such hormones bearing a bulky 17α-substituent such as a 17α-ethynyl grouping.

| STARTING MATERIAL | QUATERNARY INTERMEDIATE(CATION) | DIHYDRO DERIVATIVE |
|---|---|---|
| mestranol | | |

METHOD C

Method A is followed, except that a reactant of the formula

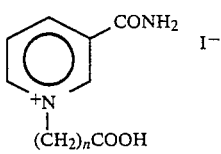

wherein n=1–3, preferably 2, is used in place of nicotinic acid. (That starting material may be prepared from nicotinamide, e.g. when n=2, by reacting 3-iodopropionic acid with nicotinamide). The quaternary salt of formula (II) thus obtained may then be reduced as described in Method A.

The representative estrogen depicted below may be derivatized in this manner to the corresponding compounds of formulas (II) and (I), as may the remaining estrogens mentioned with Method A.

Method C may be of particular use in preparing derivatives of estrogens in which the hydroxy function is hindered, e.g. mestranol.

Alternatively, Method C may follow Method A except that it employs a reactant of the formula

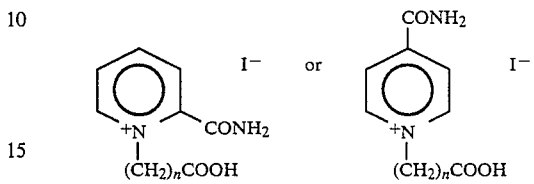

(prepared from picolinamide or isonicotinamide, e.g. when n=2, by reacting 3-iodopropionic acid with the selected amide starting material), to afford derivatives of the estrogens indicated with Method A.

| STARTING MATERIAL | QUATERNARY INTERMEDIATE(CATION) | DIHYDRO DERIVATIVE |
|---|---|---| estradiol

This compound can be subsequently selectively hydrolyzed by known methods to the corresponding 17-monoester of formula (II), which can be reduced to the corresponding preferred 17-monoester of formula (I).

METHOD D

Method A is followed, except that the drug is reacted with 3-quinolinecarboxylic acid or its acid chloride or anhydride or activated ester or quaternized activated ester instead of nicotinic acid or its acid chloride or anhydride or activated ester or quaternized activated ester.

The representative drugs depicted below may be derivatized in this manner to the correpsonding compounds of formulas (II) and (I), as may the remaining drugs mentioned with Method A.

The procedure of Method D may be repeated using 4-isoquinolinecarboxylic acid or its acid chloride or anhydride or activated ester or quaternized activated ester in place of 3-quinolinecarboxylic acid or its acid chloride or anhydride or activated ester or quaternized activated ester, to afford the corresponding derivatives of estrogens such as those indicated with Method A.

The general procedures described above may be utilized to provide the 1,2-dihydro derivatives as well as the depicted 1,4-dihydros.

| STARTING MATERIAL | QUATERNARY INTERMEDIATE(CATION) | DIHYDRO DERIVATIVE |
|---|---|---| estradiol

This compound can be subsequently selectively hydrolyzed by known methods to the corresponding 17-monoester of formula (II), which can be reduced to the corresponding preferred 17 monoester of formula (I).

| STARTING MATERIAL | QUATERNARY INTERMEDIATE(CATION) | DIHYDRO DERIVATIVE |
|---|---|---|
| 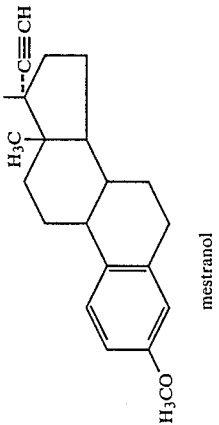 mestranol | 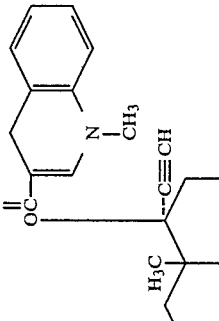 | 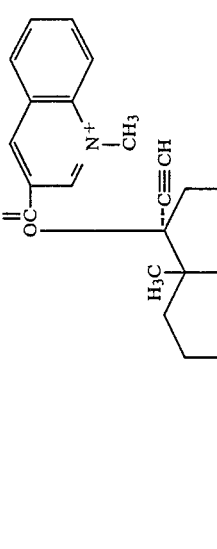 |

METHOD E

Method A is followed, except that a reactant of the formula

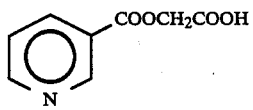

is used in place of nicotinic acid. (That starting material may be prepared by reacting nicotinic anhydride, nicotinoyl chloride or nicotinic acid with glycolic acid.)

The representative estrogen mentioned below may be derivatized in this manner to the corresponding compounds of formulas (II) and (I), as may the remaining estrogens mentioned with Method A.

Alternatively, Method E may follow Method A except that it employs a reactant of the formula

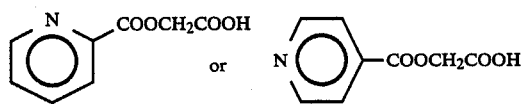

(prepared by reacting picolinic acid or its acid chloride or anhydride, or isonicotinic acid or its acid chloride or anhydride, respectively, wit glycolic acid), to afford derivatives of the estrogens indicted with Method A.

II. Method for Derivatizing —OH Functions in Estrogens with p=1 or p=2 Type Carriers

METHOD F

The estrogen is reacted with nicotinuric acid chloride, with nicotinuric acid anhydride, or with niotinuric acid in the presence of a suitable coupling agent such as dicyclohexylcarbodiimide, in an appropriate organic solvent, to afford the corresponding glycylnicotinate, or nicotinurate. The nicotinurate is then quaternized and subsequently reduced using the methods described above in Method A. When the estrogen contains more than one reactive hydroxyl function, reaction conditions may be varied so that more than one hydroxyl function will be converted to nicotinurate groupings. If more than one carrier moiety is so introduced, selective hydrolysis may be employed at a later stage in the synthetic pathway, e.g. after quaternization, to generate a derivative containing fewer carrier moieties, if such is desired.

Alternatively, the estrogen may be reacted with an activated ester of nicotinuric acid or the like, e.g. a succinimidyl ester such as

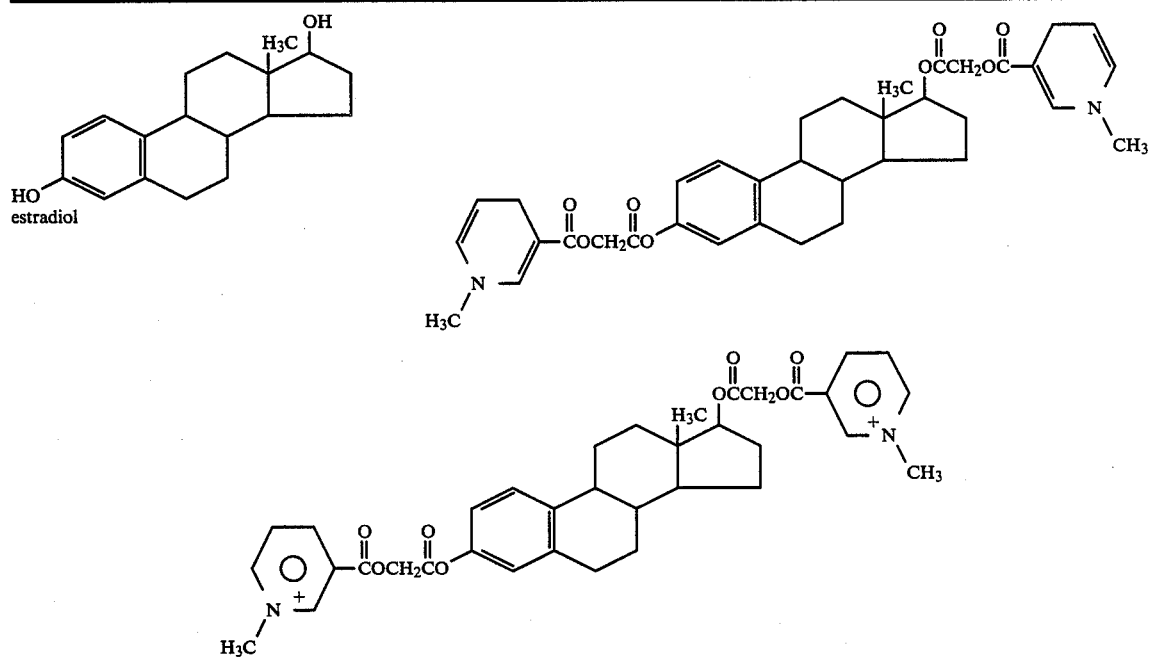

This compound can be subsequently selectively hydrolyzed by known methods to the corresponding 17-monoester of formula (II), which can be reduced to the corresponding preferred 17-monoester of formula (I).

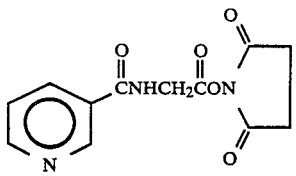

and the product quaternized and then reduced as described above. As yet another alternative, the activated ester, e.g. the succinimidyl ester depicted above, may be quaternized (e.g. by treatment with methyl iodide) and the quaternized activated ester then reacted with the estrogen. The quaternary compound of formula (II) thus obtained may then be reduced as described in Method A to give the corresponding compound of formula (I).

Alternatively, glycine may be first reacted with a reagent capable of introducing an amino protecting group such as benzyloxycarbonyl or t-butylcarbonyl and the N-protected glycine then reacted with the estrogen in the presence of a coupling agent such as dicyclohexylcarbodiimide, followed by removal of the N-protecting group, followed by reaction with nicotinoyl chloride or nicotinic anhydride, or with nicotinic acid in the presence of dicyclohexylcarbodiimide or other suitable coupling agent, to afford the nicotinurate. The nicotinurate may then be quaternized and the quaternary reduced as described in the preceding paragraph.

The representative estrogens depicted below may be derivatized in this manner to the corresponding compounds of formulas (II) and (I). Estriol and 3-monoesters and 17-monoesters of estradiol, e.g. estradiol benzoate and estradiol valerate, may be similarly derivatized, as may the other hydroxy-containing estrogens specifically mentioned in this specification.

The procedure of the third paragraph of this method may be repeated using picolinic acid or its acid chloride or anhydride, or isonicotinic acid or its acid chloride or anhydride, in place of nicotinic acid or its acid chloride or anhydride, respectively, to convert estrogens such as those specifically mentioned for derivatizing by this method to the corresponding glycyl picolinic acid esters or glycyl isonicotinic acid esters and then to the corresponding compounds of formulas (II) and (I). The procedure of the first or second paragraph of this method may be similarly adapted. Moreover, any of these procedures may be repeated, substituting a different amino acid or nicotinic acid derivative thereof for the glycine or nicotinuric acid used above, e.g. replacing glycine with alanine, valine, leucine, phenylalanine, isoleucine, methionine, asparagine or glutamine.

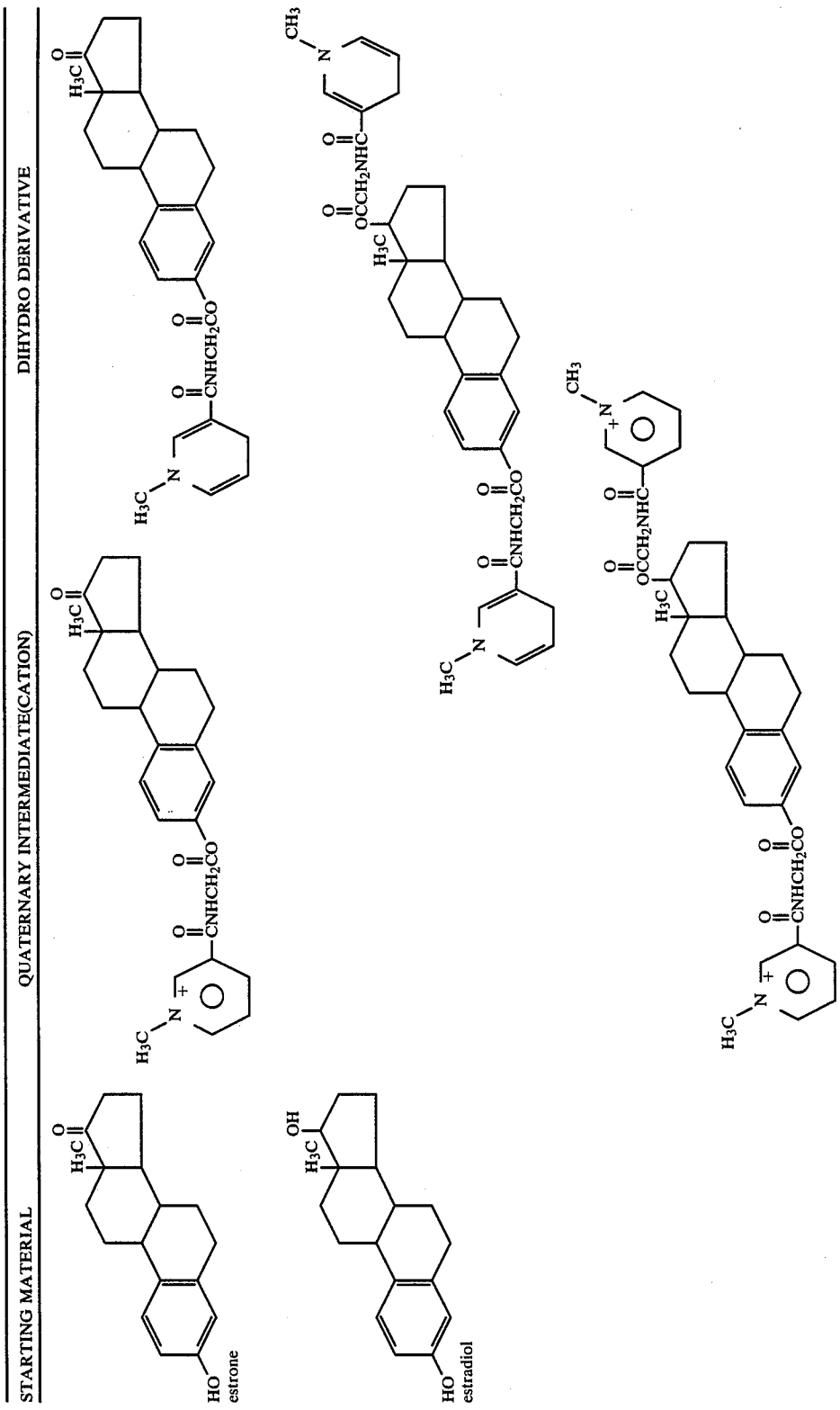
This compound can be subsequently selectively hydrolyzed by known methods to the corresponding 17-monoester of formula (II), which can be reduced to the corresponding preferred 17-monoester of formula (I).

| STARTING MATERIAL | QUATERNARY INTERMEDIATE(CATION) | DIHYDRO DERIVATIVE |
|---|---|---|
| 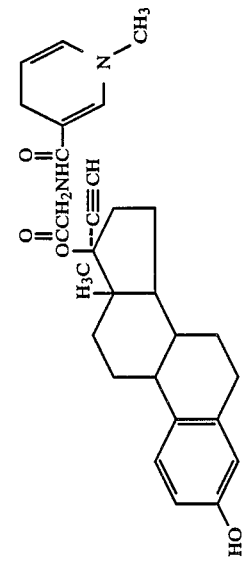<br>ethinyl estradiol | 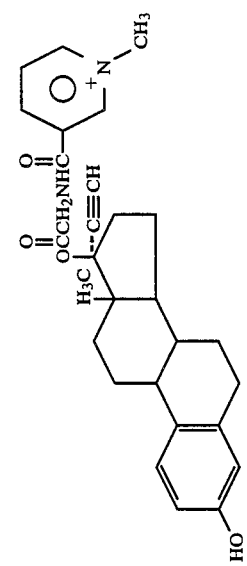 | 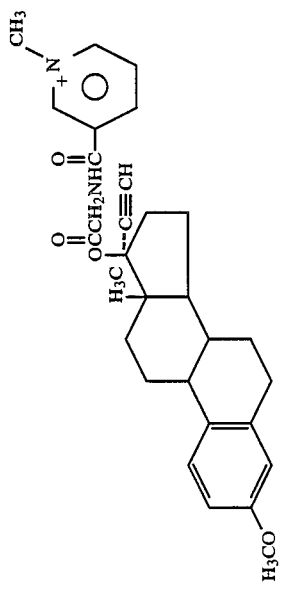 |
| 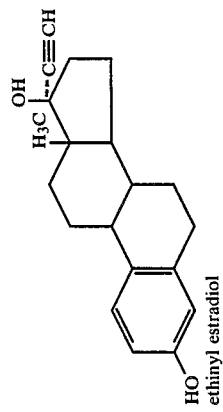<br>mestranol | 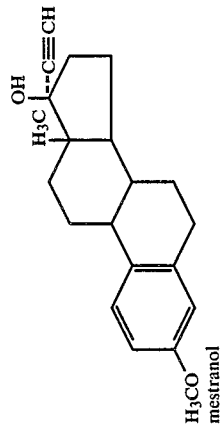 | |

| STARTING MATERIAL | QUATERNARY INTERMEDIATE(CATION) | DIHYDRO DERIVATIVE |
|---|---|---|
| 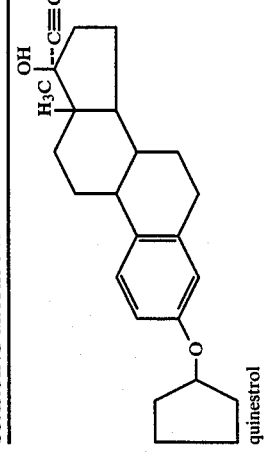 quinestrol | 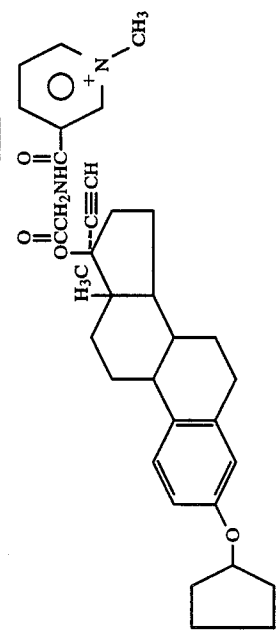 | 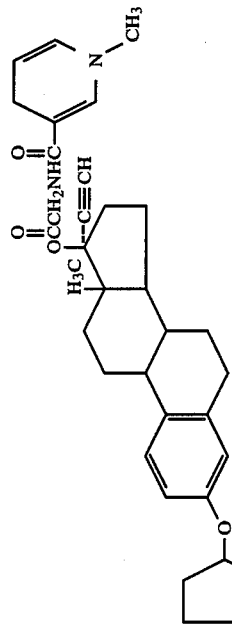 |

METHOD G

This is an alternate process for derivatizing estrogens containing secondary or tertiary hydroxyl functional groups with p=1 or 2 type carriers. According to this process, the estrogen is reacted with chloral or other aldehyde capable of forming a hemiacetal therewith. In the case of chloral, this converts the —OH function(s) to

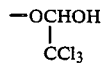

groupings. The —OH function(s) of the resultant hemiacetal can then be groups disclosed herein, e.g. by reaction with nicotinuric acid or its acid chloride or anhydride as described in Method F.

This process is analogous to Method B hereinabove and is of particular interest in connection with estrogens of the types described in paragraphs 2 and 3 of Method B.

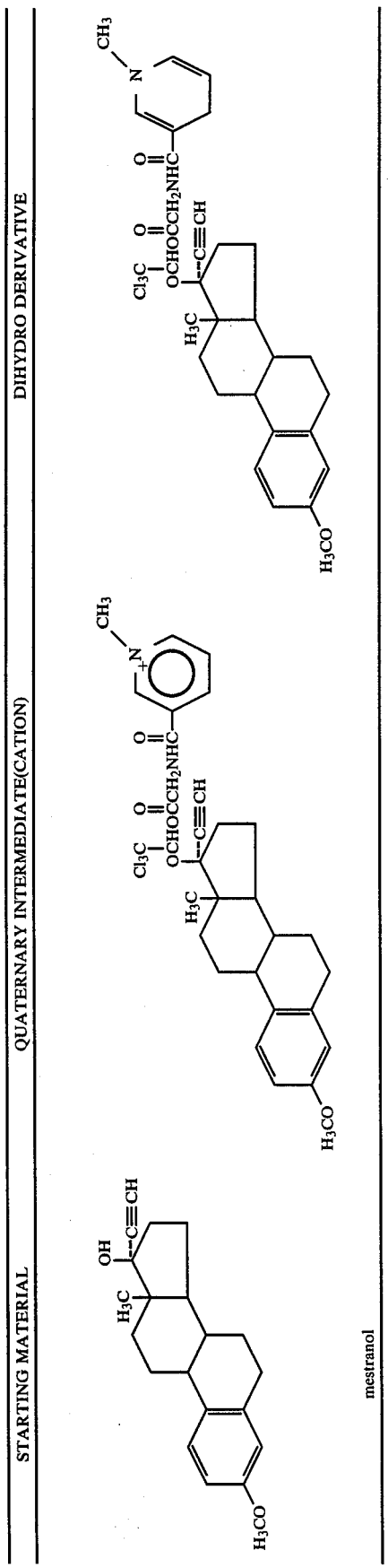

METHOD H

The procedure of the third paragraph of Method F is followed, except that a reactant of the formula

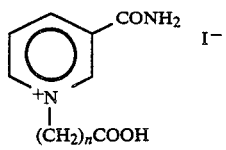

wherein n=1-3, preferably 2 (prepared as described in Method C), is used in place of nicotinic acid. The quaternary salt of formula (II) thus obtained may then be reduced as described in Method A.

The representative estrogens depicted below may be

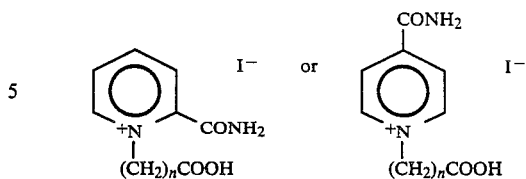

(prepared as described in Method C) in place of nicotinic acid, to afford derivatives of the drugs indicated with Method C.

The procedures of this method may be repeated, substituting a different amino acid, e.g. alanine, valine, leucine, phenylalanine, isoleucine, methionine, asparagine or glutamine, for the glycine used in the first step. (See Method F, third paragraph).

| | |
|---|---|
| STARTING MATERIAL | 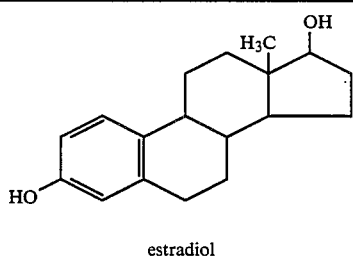<br>estradiol |
| QUATERNARY INTERMEDIATE(CATION) | 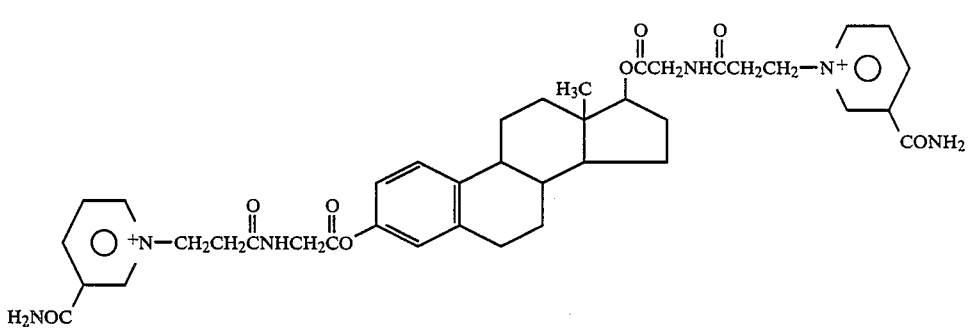 |

This compound can be subsequently selectively hydrolyzed by known methods to the corresponding 17-monoester of formula (II), which can be reduced to the corresponding preferred 17-monoester of formula (1).

| | |
|---|---|
| DIHYDRO DERIVATIVE | 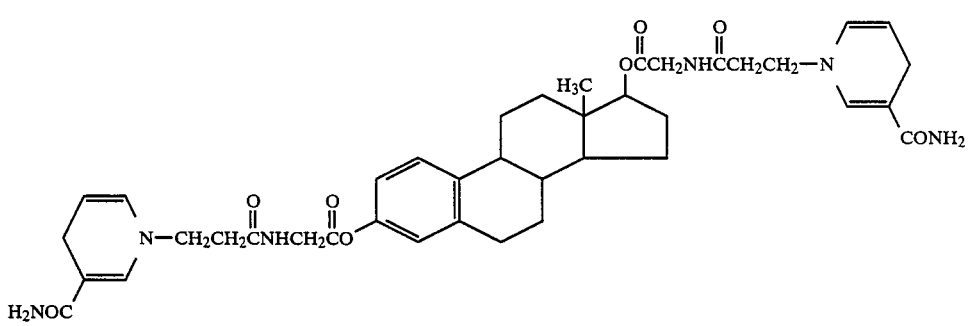 | derivatized in this manner to the corresponding compounds of formulas (II) and (I), as may the remaining estrogens indicated with Method C.

Alternatively, Method H may follow Method F, third paragraph, except that it employs a reactant of the formula

METHOD I

The procedure of Method F, third paragraph, is followed, except that removal of the N-protecting group is followed by reaction with 3-quinolinecarboxylic acid or its acid chloride or anhydride instead of nicotinic acid or its acid chloride or anhydride.

The representative estrogens depicted below may be derivatized in this manner to the corresponding compounds of formulas (II) and (I), as may the remaining estrogens mentioned with Method F.

The procedure of Method I may be repeated using 4-isoquinolinecarboxylic acid or its acid chloride or anhydride in place of 3-quinolinecarboxylic acid or its acid chloride or anhydride, to afford the corresponding derivatives.

The general procdures described above may be utilized to provide the 1,2-dihydro derivatives as well as the depicted 1,4-dihydros.

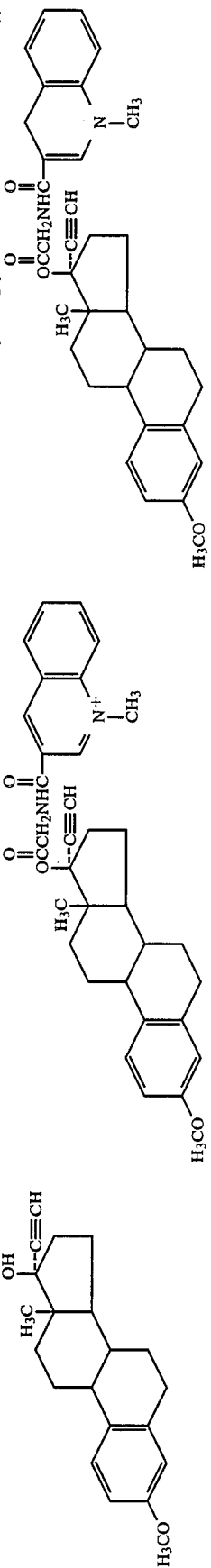

METHOD J

The procedure of the third paragraph of Method F is followed, except that a reactant of the formula

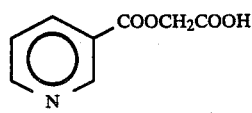

is used in place of nicotinic acid.

The representative estrogen depicted below may be derivatized in this manner to the corresponding compounds of formulas (II) and (I), as may the remaining estrogens mentioned with Method F.

Alternatively, Method J may follow Method F, third paragraph, except that it employs a reactant of the formula

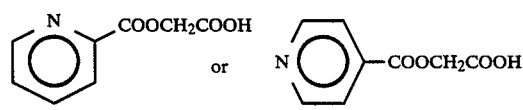

(prepared as described in Method E), to afford derivatives of the estrogens indicated with Method F.

The procedure of the first or third paragraph of this method may be repeated, substituting a different amino acid, e.g. alanine, valine, leucine, phenylalanine, isoleucine, methionine, asparagine or glutamine, for the glycine used in the first step. (see Method F, third paragraph).

| | |
|---|---|
| STARTING MATERIAL | 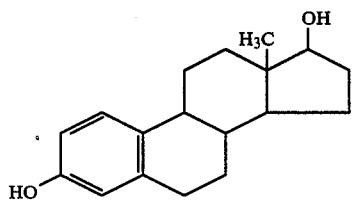<br>estradiol |
| QUATERNARY INTERMEDIATE-(CATION) | 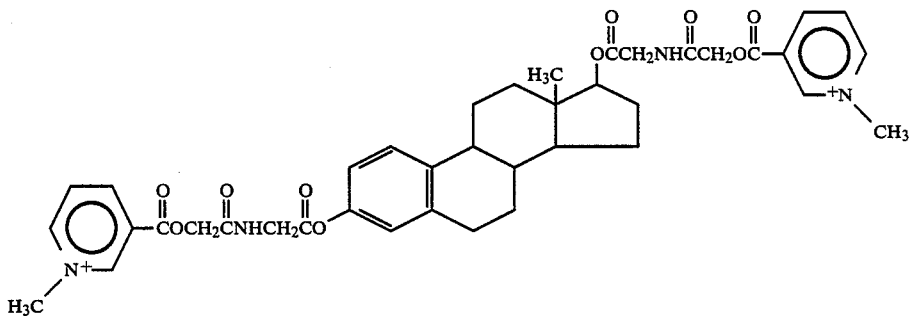 |
| | This compound can be subsequently selectively hydrolyzed by known methods to the corresponding 17-monoester of formula (II), which can be reduced to the corresponding preferred 17-monoester of formula (I). |
| DIHYDRO DERIVATIVE | 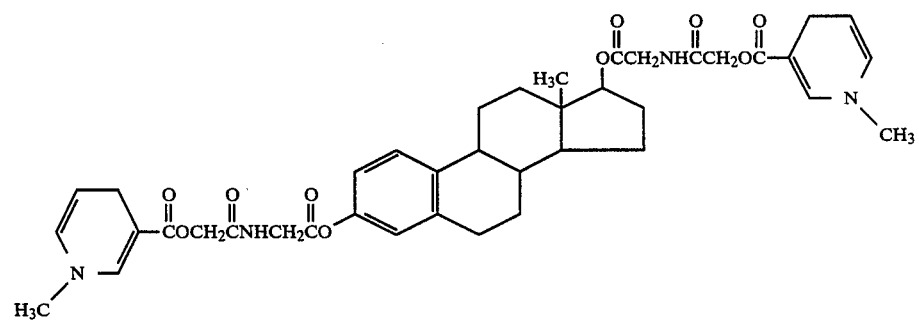 |

III. Method for Salt Formation

An ether solution of a compound of formula (I) is treated with an equivalent amount of anhydrous p-toluenesulfonic acid dissolved in dry ether. Mixing at room temperature is continued until the imminium salt precipitates out of solution. The salt is then removed by filtration.

SYNTHETIC EXAMPLES

In order to further illustrate the compounds useful in the method and compositions of this invention, the following synthetic examples are given, it being understood that the same are intended only as illustrative.

In the examples immediately to follow, all melting points were taken on a Mel-Temp apparatus and are not

EXAMPLE 1

Preparation of
3-Nicotinoyloxyestra-1,3,5(10)-trien-17-one (Estrone Nicotinate)

To nicotinic acid (41 g, 0.333 mol) at 0° C. was added thionyl chloride (115 ml, 1.58 mol) with stirring. The mixture was refluxed for one hour, and the white crystalline product was filtered and washed sparingly with dry benzene. Excess thionyl chloride was azeotroped off with dry benzene immediately before use. Yield 90% (53.97 g) of nicotinoyl chloride hydrochloride; NMR, IR identical with literature values.

To nicotinoyl chloride hydrochloride (2.65 g, 0.015 mol) in pyridine (20 ml) at 0° C. was added estrone (2 g, 0.0074 mol). The mixture was refluxed for one hour and then poured over 100 ml of ice cold water, filtered, and dried over $P_2O_5$ under vacuum. Yield 72% (2.0076 g), m.p. 207°–210° C. Anal. calculated for $C_{24}H_{25}NO_3$; C, 76.76; H, 6.72; N, 3.73. Found: C, 76.37; H, 6.96; N, 3.67. The product is further characterized by the structural formula:

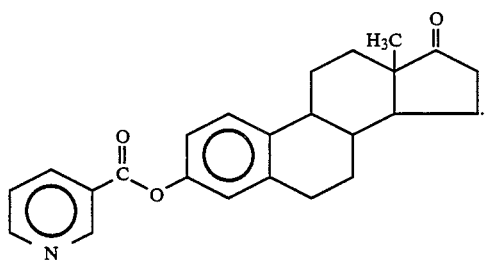

EXAMPLE 2

Preparation of
3-[(1-Methyl-3-pyridinium)carbonyloxy]estra-1,3,5(10)-trien-17-one iodide To estrone nicotinate (0.5 g, 0.0013 mol) in acetone (20 ml) was added methyl iodide (1 ml, 0.016 mol) and the mixture was refluxed overnight. The deep yellow precipitate was filtered, washed with acetone, and dried. Yield 90% (0.6226 g); m.p. 245°–248° C. (dec.). Anal. calculated for $C_{25}H_{28}NO_3I$: C, 58.03; H, 5.47; H, 2.71. Found: C, 58.16; H, 5.51; N, 2.67. The product has the formula:

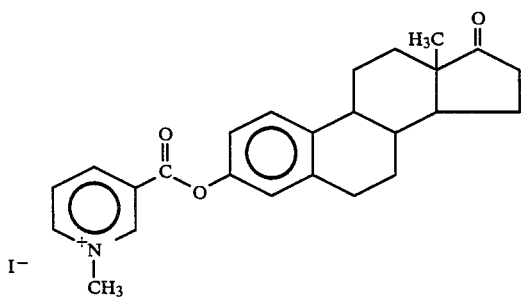

EXAMPLE 3

Preparation of
3-[(1-Methyl-1,4-dihydro-3-pyridinyl)carbonyloxy]estra-1,3,5(10)-trien-17-one To 3-[(1-methyl-3-pyridinium)carbonyloxy]estra-1,3,5(10)-trien-17-one iodide (0.600 g, 1.16 mmol) in a 50:50 mixture of methanol and deaerated water (80 ml) were added $NaHCO_3$ (0.58 g, 7.0 mmol) and $Na_2S_2O_4$ (0.81 g, 4.6 mmol). The mixture was stirred under $N_2$ for 2 hours. The precipitate was filtered, dissolved in methanol at room temperature, filtered, and then re-precipitated with deaerated water. This precipitate was then filtered and dried over $P_2O_5$ under vacuum. Yield 67% (0.3029 g). The product decomposes over the range 130°–180° C. Anal. calculated for $C_{25}H_{29}NO_3$ ($+\frac{1}{2}$ $H_2O$): C, 74.96; H, 7.56; N, 3.50. Found: C, 75.44; H, 7.271 N, 3.38. The product is further characterized by the structural formula:

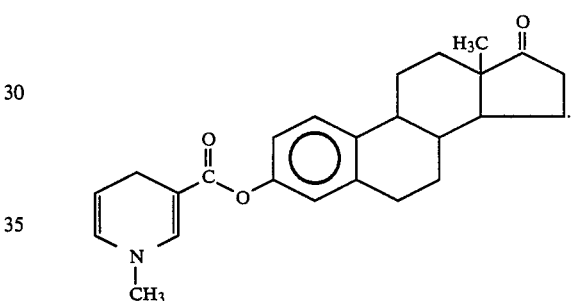

EXAMPLE 4

Preparation of
17β-Nicotinoyloxyestra-1,3,5(10)-trien-3-ol 3-methyl ether

To nicotinoyl chloride hydrochloride (3.15 g, 0.017 mol) in pyridine (20 ml) at 0° C. was added estradiol 3-methyl ether (2 g, 0.0070 mol). After refluxing one hour, the mixture was poured over 100 ml of ice water, filtered and dried over $P_2O_5$ under vacuum. Yield 76% (2.0674 g), m.p. 140°–142° C. Anal. calculated for $C_{25}H_{29}NO_3$: C, 76.68; H, 7.48; N, 3.58. Found: 76.49; H, 7.50; N, 3.55. The product has the formula:

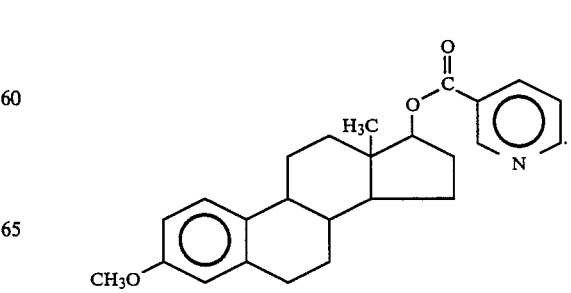

EXAMPLE 5

Preparation of 17β-[(1-Methyl-3-pyridinium)carbonyloxy]estra-1,3,5(10)-trien-3-ol 3-methyl ether iodide To 17β-nicotinoyloxyestra-1,3,5(10)-trien-3-ol 3-methyl ether (1.5 g, 0.0038 mol) in acetone (20 ml) was added methyl iodide (1 ml, 0.016 mol) and the mixture was refluxed overnight. The pale yellow precipitate was filtered, washed with acetone, and dried. Yield 76% (1.5595 g), m.p. 230°–234° C. (dec.). Anal. calculated for $C_{26}H_{32}NO_3I$: C, 58.53; H, 6.06; N, 2.63. Found: C, 58.25; H, 6.07; N, 2.59. The title compound has the formula:

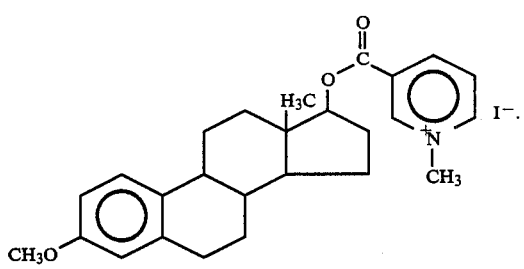

EXAMPLE 6

Preparation of 17β-[(1-Methyl-1,4-dihydro-3-pyridinyl)carbonyloxy]estra-1,3,5(10)-trien-3-ol 3-methyl ether To 17β-[(1-methyl-3-pyridinium)carbonyloxy]estra-1,3,5(10)-trien-3-ol 3-methyl ether (0.600 g, 1.12 mmol) in a 50:50 mixture of methanol and deaerated water (80 ml) were added NaHCO$_3$ (0.57 g, 6.7 mmol) and Na$_2$S$_2$O$_4$ (0.78 g, 4.6 mmol). The mixture was stirred under N$_2$ for 2 hours. The precipitate was filtered, dissolved in methanol at room temperature, filtered, and then reprecipitated with deaerated water. This precipitate was then filtered and dried over P$_2$O$_5$ under vacuum. Yield 74% (0.3383 g). The product decomposes over the range 120°–170° C. Anal. calculated for $C_{26}H_{33}NO_3$: C, 76.61; H, 8.18; N, 3.44. Found: C, 76.75; H, 8.43; N, 3.37. The product is further characterized by the structural formula:

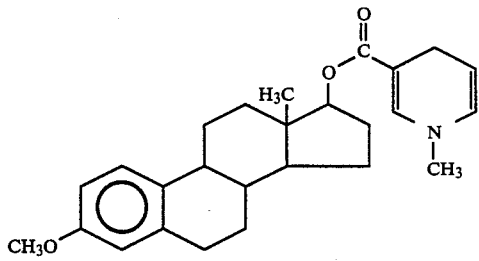

EXAMPLE 7

Preparation of Estra-1,3,5(10)-triene-3,17β-diol 3,17-dinicotinate (Estradiol 3,17β-dinicotinate)

Estradiol (2 g, 0.0073 mol) was added to nicotinoyl chloride hydrochloride (5.3 g, 0.029 mol) in dry pyridine (30 ml) at 0° C. The mixture was refluxed for 1 hour and then poured over 100 ml of ice water, filtered and dried over P$_2$O$_5$ under vacuum. Yield 90% (3.18 g), m.p. 148°–150° C. Anal. calculated for $C_{30}H_{31}N_2O_4$: C, 74.50; H, 6.47; N, 5.79. Found: C, 74.40; H, 6.32; N, 5.75. The product has the formula:

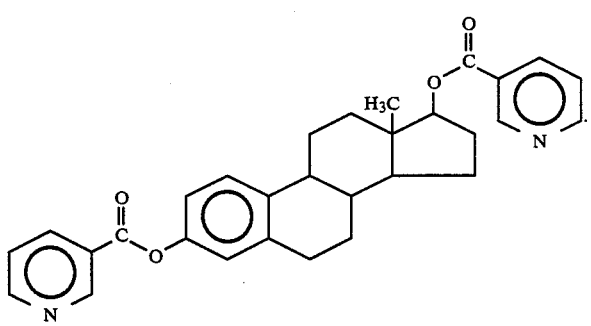

EXAMPLE 8

Preparation of 3,17β-Bis-[(1-methyl-3-pyridinium)carbonyloxy]estra-1,3,5(10)-triene diiodide Methyl iodide (1 ml, 0.016 mol) was added to estradiol 3,17β-dinicotinate (1 g, 0.0021 mol) in acetone (20 ml) and the mixture was refluxed overnight. The deep yellow precipitate which formed was filtered, washed with acetone, and dried. Yield 72% (1.262 g), m.p. 256°–258° C. (dec.). Anal. calculated for $C_{32}H_{36}N_2O_4I_2$ (+1 H$_2$O): C, 48.99; H, 4.89; N, 3.57. Found: C, 48.78; H, 4.66; N, 3.63. The product is further characterized by the structural formula:

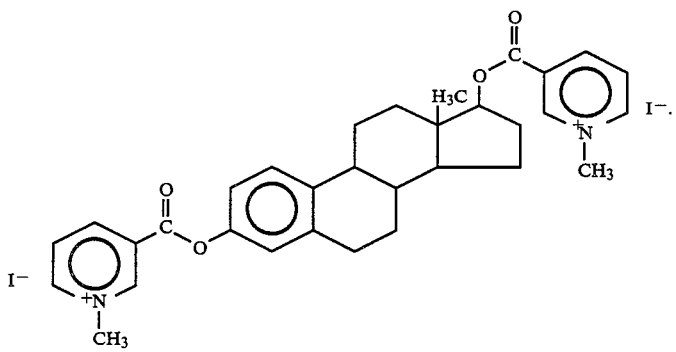

That compound was converted to the corresponding 3-hydroxy steroid of the formula

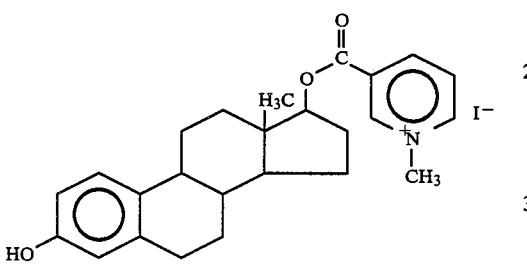

by partial hydrolysis; the resultant 3-hydroxy compound was then reduced, as generally described hereinabove, to afford the corresponding dihydro derivative of the formula

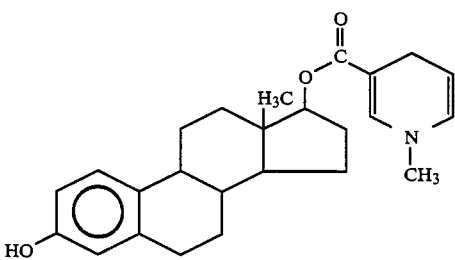

EXAMPLE 9

Preparation of Estra-1,3,5(10)-triene-3,17β-diol 17-nicotinate (Estradiol 17β-nicotinate)

0.5% Potassium bicarbonate in 95% methanol (60 ml) was added to estradiol 3,17β-dinicotinate (0.5 g, 0.0010 mol) and the slurry was stirred overnight at room temperature. Water (60 ml) was added and repeated extractions into chloroform were made, combined and dried over anhydrous sodium sulfate. The chloroform was removed in vacuo and the resulting pinkish-white solid was suspended in methanol at room temperature. The white powder thus obtained was separated by filtration and dried. Yield 94% (0.3663 g), m.p. 221°–222° C. Anal. calc. for $C_{24}H_{27}NO_3$: C, 76.36; H, 7.22; N, 3.71. Found: C, 76.20; H, 7.25; N, 3.70. The product has the formula:

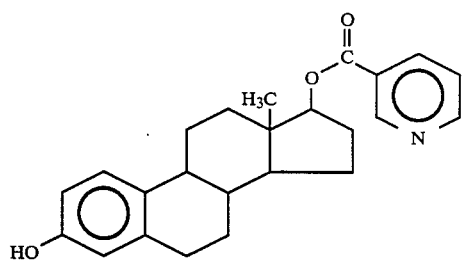

EXAMPLE 10

Preparation of 17β-[(1-Methyl-3-pyridinium)carbonyloxy]estra-1,3,5(10)-trien-3-ol iodide Methyl iodide (2 ml, 0.032 mol) was added to estra-1,3,5(10)-triene-3,17β-diol 17-nicotinate (2.0953 g, 0.0056 mol) in acetone (200 ml) and the mixture was refluxed overnight. The pale yellow precipitate which formed was removed by filtration, washed with acetone and dried. Yield 83% (2.4203 g), m.p. 268°–272° C. (dec.). Anal. calculated for $C_{25}H_{29}NO_3I$: C, 57.92; H, 5.65; N, 2.70. Found: C, 57.70; H, 5.73; N, 2.68. The product has the formula:

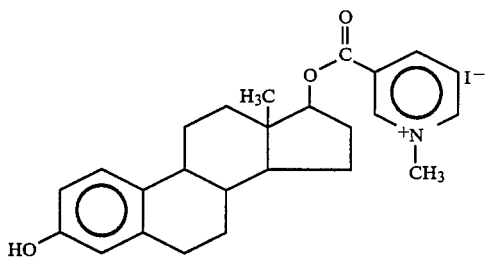

EXAMPLE 11

Preparation of 17β-[(1-Methyl-1,4-dihydro-3-pyridinyl)carbonyloxy]estra-1,3,5(10)-trien-3-ol To 17β-[(1-methyl-3-pyridinium)carbonyloxy]estra-1,3,5(10)-trien-3-ol iodide (1.09 g, 0.0021 mol) in 50:50 t-butanol/deaerated water (150 ml) were added NaHCO₃ (1.06 g, 0.0126 mol) and $Na_2S_2O_4$ (1.46 g, 0.0084 mol). The mixture was stirred under N₂ for one hour. The precipitate which formed was removed by filtration, dissolved in ether and dried over anhydrous Na₂SO₄. The ether was removed in vacuo. Yield 64% (0.2416 g). The product decomposes over the range 115°–130° C. Anal. calculated for $C_{25}H_{31}NO_3$ (+½ $H_2O$): C, 74.59; H, 8.03; N, 3.48. Found: C, 74.57; H, 8.04; N, 3.40. The product is characterized by the structural formula:

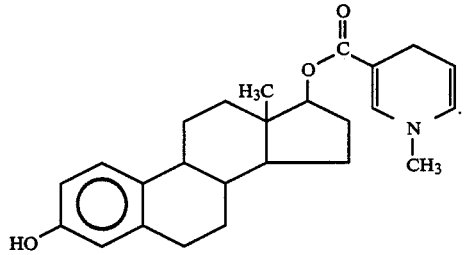

EXAMPLE 12

Preparation of 3-Benzoyloxy-17β-nicotinoyloxyestra-1,3,5(10)-triene [Estra-1,3,5(10)-triene-3,17β-diol 3-benzoate 17-nicotinate]

Repetition of the general procedure of EXAMPLE 4, substituting an equivalent quantity of estradiol benzoate for the estradiol 3-methyl ether there employed, affords the title compound having the structural formula:

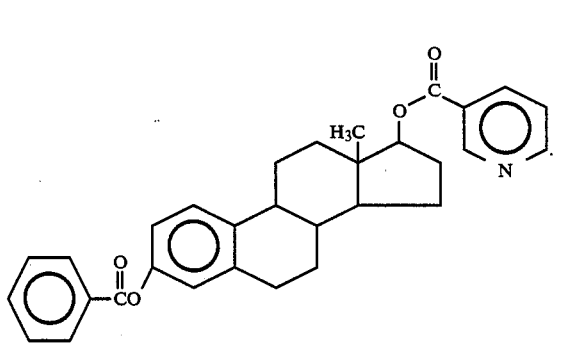

EXAMPLE 13

Preparation of 3-Benzoyloxy-17β-[(1-methyl-3-pyridinium)carbonyloxy]estra-1,3,5(10)-triene iodide When the general procedure of EXAMPLE 5 is repeated, substituting an equivalent quantity of 3-benzoyloxy-17β-nicotinoyloxyestra-1,3,5(10)-triene for the steroidal starting material utilized therein, there is obtained the title compound which has the structural formula:

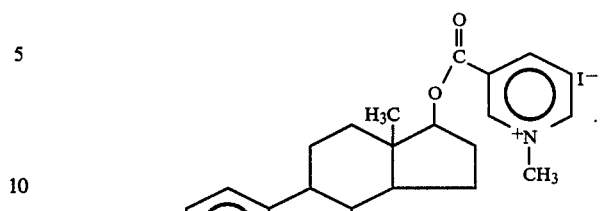

EXAMPLE 14

Preparation of 3-Benzoyloxy-17β-[(1-methyl-1,4-dihydro-3-pyridinyl)carbonyloxy]estra-1,3,5(10)-triene The general procedure of EXAMPLE 6 is repeated, substituting an equivalent quantity of 3-benzoyloxy-17β-[(1-methyl-3-pyridinium)carbonyloxy]estra-1,3,5(10)-triene iodide for the steroidal starting material there employed. Obtained in this manner is the title compound, which has the structural formula:

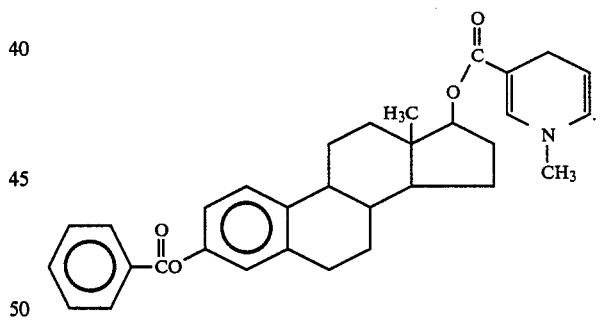

EXAMPLE 15

Preparation of 3,17β-Bis-[(1-methyl-1,4-dihydro-3-pyridinyl)carbonyloxy]estra-1,3,5(10)-triene Reduction of 3,17β-bis-[(1-methyl-3-pyridinium)carbonyloxy]estra-1,3,5(10)-triene diiodide (the product of EXAMPLE 8) with sodium dithionite as generally described hereinabove affords the title compound of the structural formula:

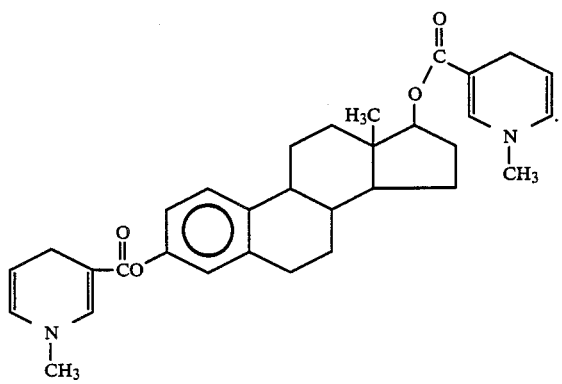

EXAMPLE 16

Preparation of
17β-Ethynylestra-1,3,5(10)-triene-3,17β-diol
3,17-dinicotinate

Ethinyl estradiol is reacted with nicotinic anhydride as generally described hereinabove. Obtained in this manner is the title compound of the formula:

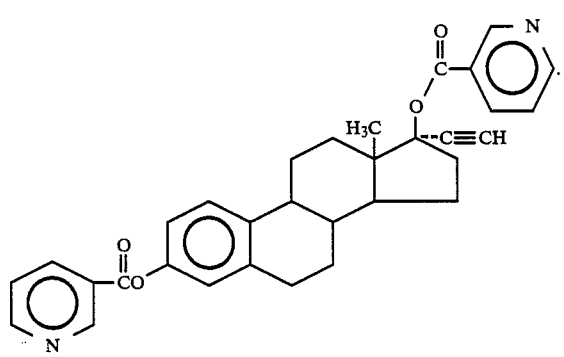

EXAMPLE 17

Preparation of
17β-Ethynylestra-1,3,5(10)-triene-3,17β-diol
17-nicotinate

The product of EXAMPLE 16 is subjected to preferential phenolic hydrolysis, affording the title compound having the structural formula:

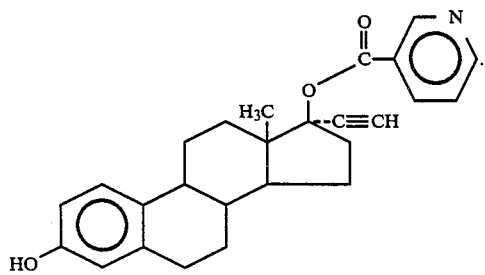

EXAMPLE 18

Preparation of
17β-Ethynyl-3-hydroxy-17β-[(1-methyl-3-pyridinium)-carbonyloxy]estra-1,3,5(10)-triene iodide When the product of EXAMPLE 17 is reacted with methyl iodide according to the general procedure of EXAMPLE 2, the title compound is obtained. It has the structural formula:

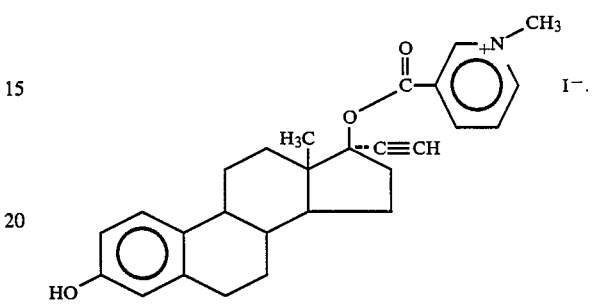

EXAMPLE 19

Preparation of
17β-Ethynyl-17β-[(1-methyl-1,4-dihydro-3-pyridinyl)-carbonyloxy]estra-1,3,5(10)-trien-3-ol The product of EXAMPLE 18 is subjected to reduction with sodium dithionite according to the general procedure of EXAMPLE 11. Obtained in this manner is the title compound, characterized by the structural formula:

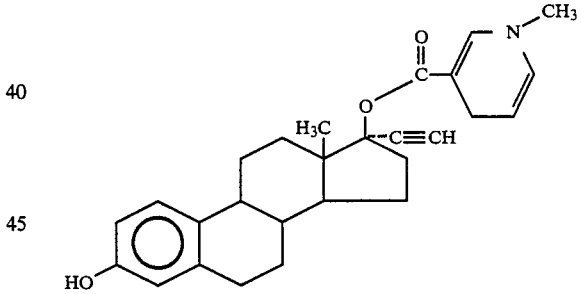

PHARMACOLOGICAL TESTING METHOD

Adult male Sprague-Dawley rats (Charles River Breeding Laboratories, Wilmington, MA) were used for this study. Animals were maintained singly in wire-bottom cages under controlled light (14 hour light, 10 hour dark; lights off at 1100 hours) and temperature (23° C.). Animals received Purina rat chow and tap water ad libitum.

Behavioral Screening Tests

All animals were tested for sexual behavior prior to orchidectomy and drug administration. Testing was performed in rectangular Plexiglas ® arenas (31 cm×30 cm×36 cm) in a dimly lit room (7 watt bulb). All testing procedures occurred between 1300 and 1700 hours. The test male was placed into an arena for 5 minutes prior to the introduction of a female via the top of the chamber. The stimulus female (ovariectomized) was rendered sexually receptive by a subcutaneous (s.c.) injection of 100 μg of estradiol benzoate and 500 μg of progesterone in 0.1 ml of corn oil, 48 and 4 hours prior to testing. Each mount, intromission and ejaculation was recorded on an event recorder (Lafayette Instrument Co., Lafayette, IN; model 56041). Each male was tested every 5 days until four successive and consistent behavioral patterns were achieved. In addition to copulatory tests, males were tested for penile erection reflexes [Davidson et al, Physiology & Behavior, Vol. 21, pp. 171–146 (1978)]. Erectile tests were performed 24 hours before copulatory events every 5 days. After copulatory behavior parameters were deemed satisfactory, animals were bilaterally orchidectomized via a single mid-ventral incision and rehoused for 28 days with no further behavioral testing.

Full Behavioral Tests

After rats were randomly divided among experimental groups, they received an equimolar dose of $E_2$-CDS (3 mg/kg) or $E_2$-VAL (2.7 mg/kg) or the vehicle (DMSO, 0.5 ml/kg) via a single tail vein injection. Testing was performed as described above and the following parameters were calculated from the record: mount latency (ML), the time from the introduction of the female to the initial mount or intromission; intromission latency (IL), the time from the introduction of the female to the first intromission; ejaculation latency (EL), the time from the first intromission to ejaculation; and postejaculatory interval (PEI), the time from ejaculation to the first intromission of the next copulatory series. Tests were terminated and considered negative if intromission latency exceeded 15 minutes, ejaculation latency exceeded 30 minutes or postejaculatory interval exceeded 15 minutes. Mounting frequency and intromission frequency were also assessed. Copulatory and penile reflex tests were performed at 3, 7, 14, 21, 28, 35 and 42 days after administration of the drugs.

Statistical Treatment

Mean values and standard errors of the mean were calculated for data and analyzed by analysis of variance and Student-Newman-Keuls statistics (full behavior data; Zar, BIOSTATISTICAL ANALYSIS, Prentice-Hall, Inc., Englewood Cliffs, NJ, 1974). Data concerning percent of animals responding to a treatment were analyzed by the Fisher Exact test (Zar, supra). The level of probability for all tests was <0.05.

RESULTS

The effects of $E_2$-CDS (▨), $E_2$-VAL (◻) and DMSO (■) on mounting behavior from day 0 to day 35 are depicted in FIG. 1. Results were analyzed by the Fisher Exact test and differences are denoted in FIG. 1 as follows: (a) different from DMSO, $p<0.05$; (b) different from $E_2$-VAL, $p<0.05$. As shown in FIG. 1, $E_2$-CDS restored mounting behavior in 100% of the animals by day 3 and was greater than DMSO controls from 2 through 5 weeks. At no time after its administration did $E_2$-VAL fully restore mounting behavior, with only 2 rats responding by 14 days.

Figure 2:
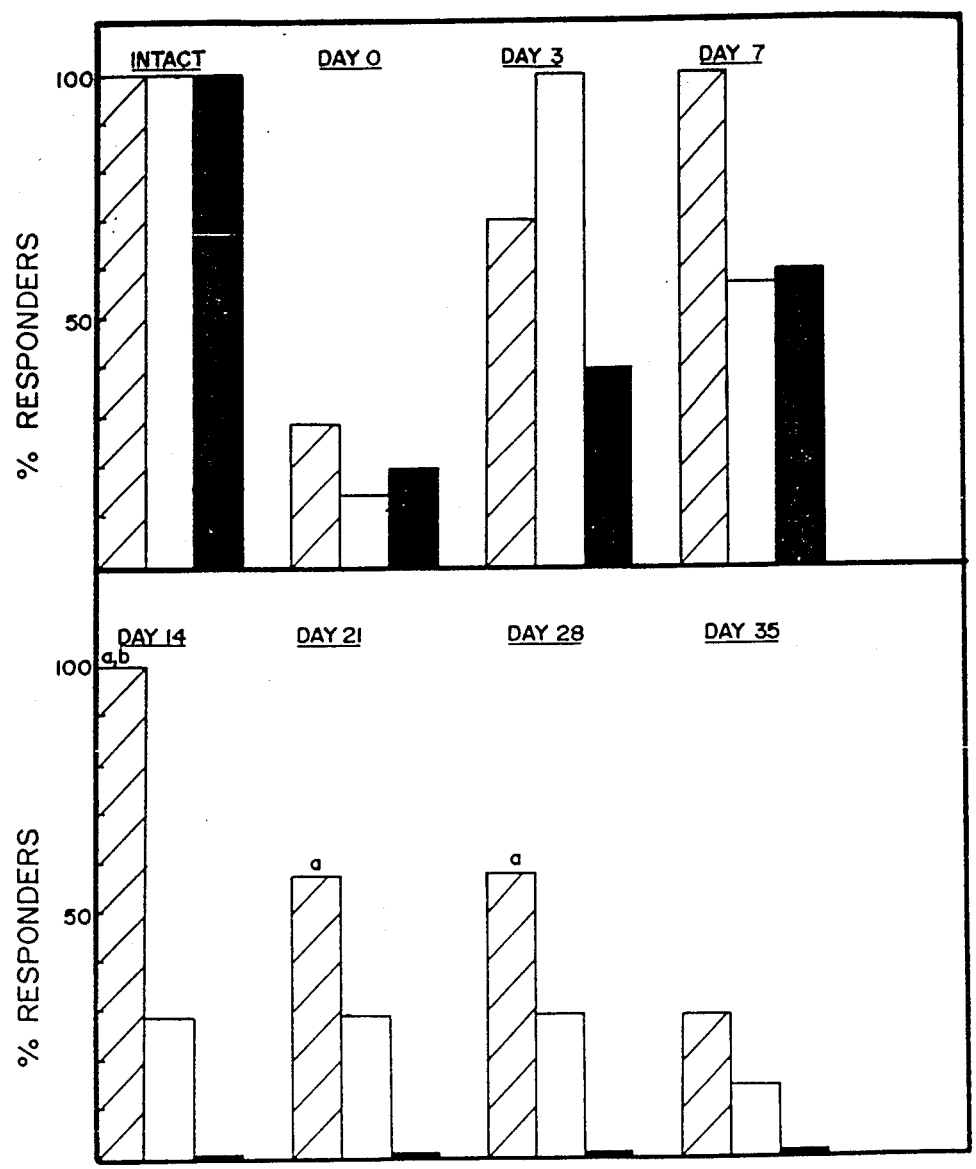
FIG. 2 is a bar graph illustrating the effects of $E_2$-CDS ( ▨ ), $E_2$-VAL (□) and DMSO ( ■ ) on the intromission percentage (percent responders) in castrated male rats from day 0 to day 35 after a single i.v. injection.

The effects of $E_2$-CDS (▨), $E_2$-VAL (◻) and DMSO (■) on intromission behavior from day 0 to day 35 are depicted in FIG. 2. Results were analyzed and differences denoted as in FIG. 1. As shown in FIG. 2, $E_2$-VAL fully restored intromission behavior by three days, rapidly waned at 1 week, and at no time differed from control levels. On the other hand, all $E_2$-CDS treated rats intromitted by 7 days and to a greater extent than either $E_2$-VAL or DMSO-treated animas by 2 weeks. More than 50% of rats receiving $E_2$-CDS displayed intromission behavior as long as 21 days and returned to control levels by 5 weeks.

Figure 3:
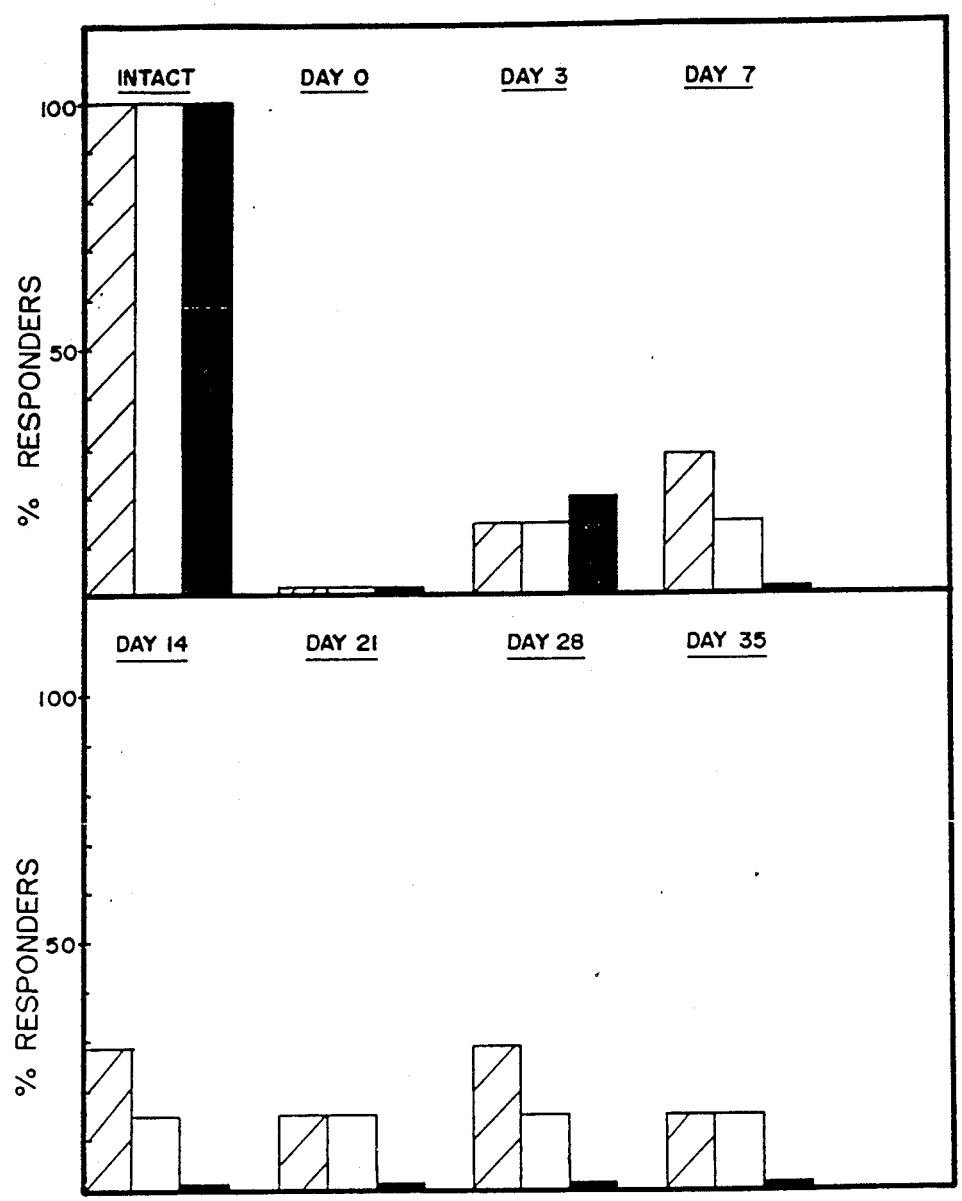
FIG. 3 is a bar graph illustrating the effects of $E_2$-CDS ( ▨ ), $E_2$-VAL (□) and DMSO ( ■ ) on the ejaculation percentage (percent responders) in castrated male rats from day 0 to day 35 after a single i.v. injection.

FIG. 3 depicts the effects of $E_2$-CDS (▨), $E_2$-VAL (◻) and DMSO (■) on ejaculation from day 0 to day 35. Results were analyzed by the Fisher Exact test, as in FIGS. 1 and 2. None of the three groups was significantly different from the others at any time examined. Ejaculation response was not induced by either $E_2$-CDS or $E_2$-VAL and no more than 2 rats in any of the experimental groups ejaculated.

Figure 4:
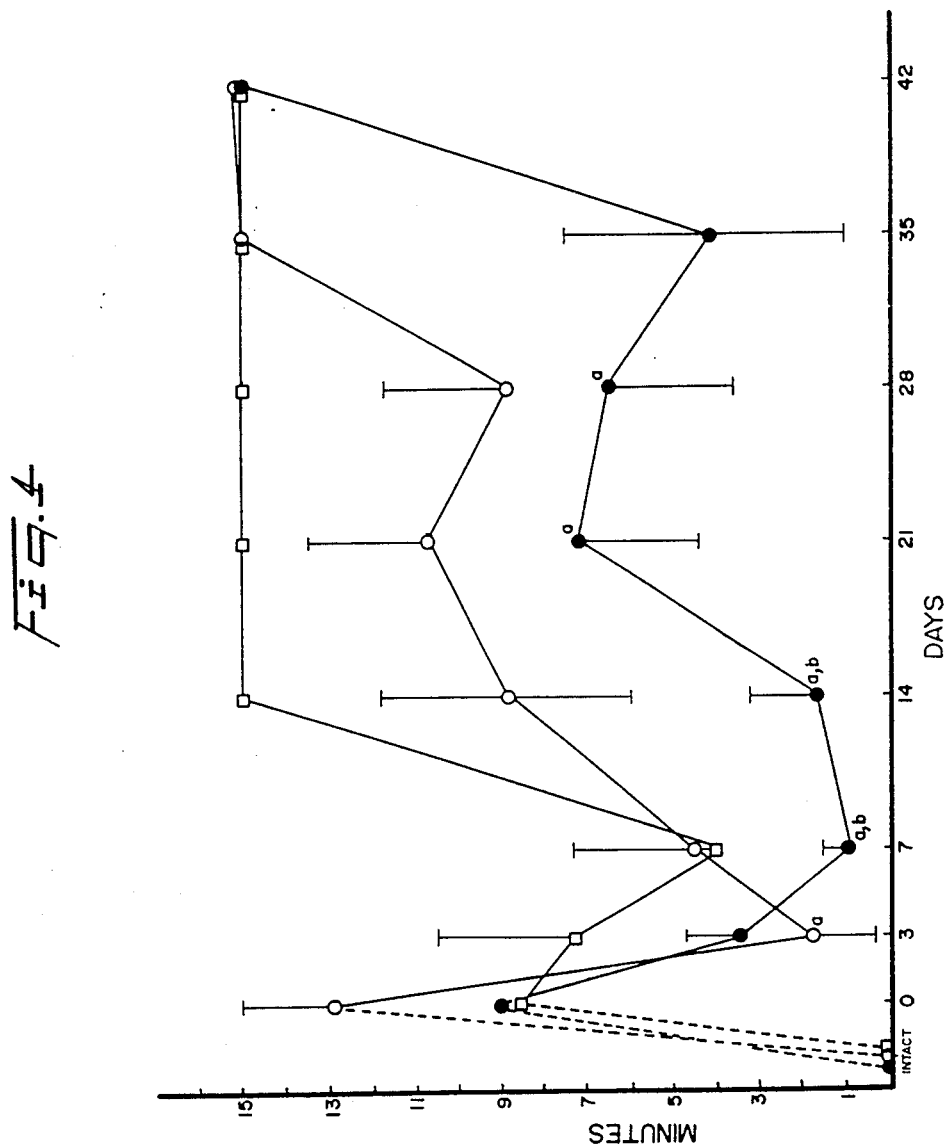
FIG. 4 is a plot of mean mounting latency, in minutes, versus time, in days, following a single i.v. injection of $E_2$-CDS ( ● ), $E_2$-VAL ( ○ ) or DMSO (□) to castrated male rats.

The effects of $E_2$-CDS (●), $E_2$-VAL (○) and DMSO (◻) on mounting latency from day 0 to day 42 are shown in FIG. 4. Results were analyzed by ANOVA and Student-Newman-Keuls statistics and differences are denoted as follows: (a) different from DMSO, $p<0.05$; (b) different from $E_2$-VAL, $p<0.05$. As depicted in FIG. 4, mounting latency was sharply reduced by 3 days after administration of either $E_2$-CDS or $E_2$-VAL. The mounting latency of $E_2$-CDS rats continued to be less than the control through 28 days and less than $E_2$-VAL through 2 weeks. In comparison, these mounting latency of animals treated with $E_2$-VAL returned to control levels by 7 days.

Figure 5:
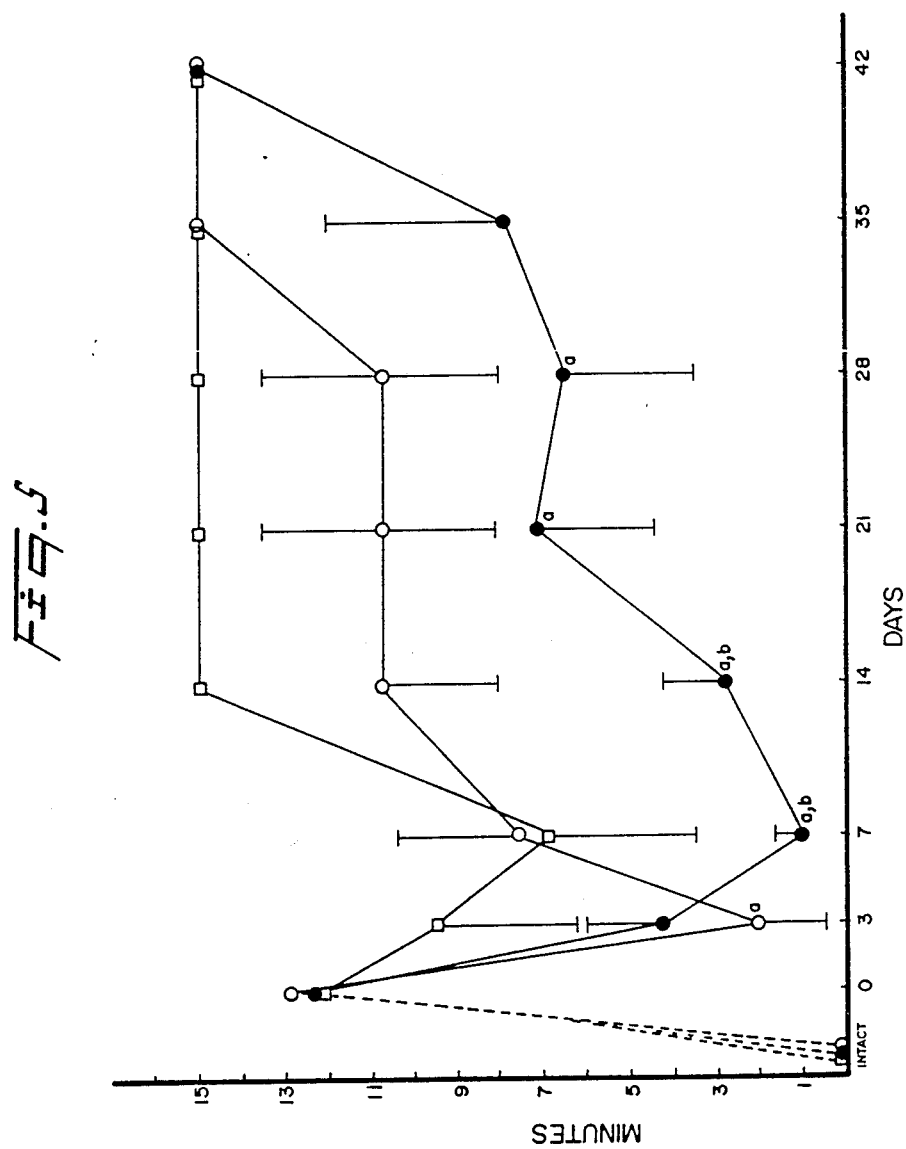
FIG. 5 is a plot of mean intromission latency, in minutes, versus time, in days, following a single i.v. injection of $E_2$-CDS ( ● ), $E_2$-VAL ( ○ ) or DMSO (□) to castrated male rats.

The effects of $E_2$-CDS (●), $E_2$-VAL (○) and DMSO (◻) on intromission latency from day 0 to day 42 are depicted in FIG. 5. Results were analyzed by ANOVA and Student-Newman-Keuls statistics and differences are denoted as follows: (a) different from DMSO, $p<0.05$; (b) different from $E_2$-VAL, $p<0.05$. FIG. 5 shows that intromission latency was affected similarly to mounting latency. $E_2$-CDS and $E_2$-VAL reduced intromission latency by 3 days. $E_2$-VAL lost its effectiveness by 1 week while $E_2$-CDS intromission latency continued to be less than control intromission latency through 4 weeks.

Figure 6:
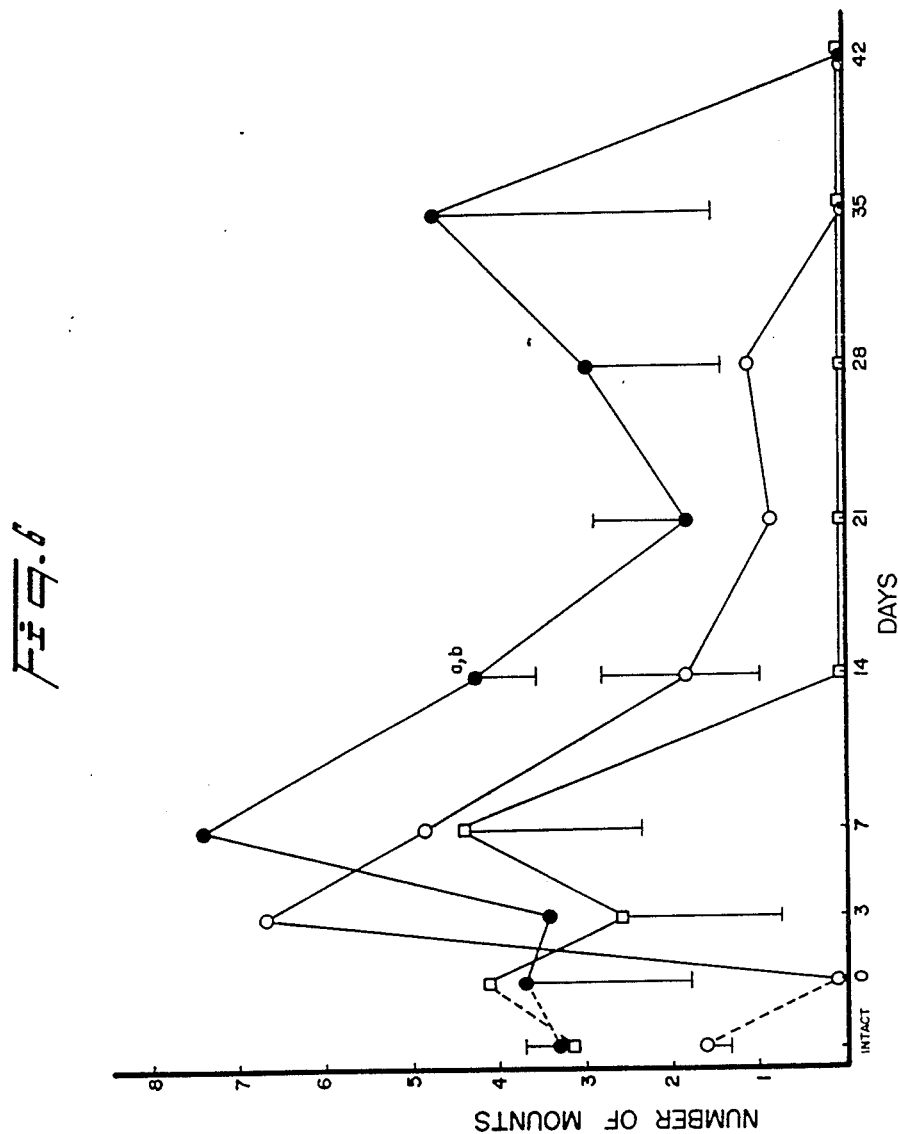
FIG. 6 is a plot of mean mounting frequency, per minute, versus time, in days, following a single i.v. injection of $E_2$-CDS ( ● ), $E_2$-VAL ( ○ ) or DMSO (□) to castrated male rats.

FIG. 6 depicts the effects of $E_2$-CDS (●), $E_2$-VAL (○) and DMSO (◻) on mounting frequency from day 0 to day 42. Results were analyzed by ANOVA and Student-Newman-Keuls statistics and differences are denoted as follows: (a) different from DMSO, $p<0.05$; (b) different from $E_2$-VAL, $p<0.05$. Mounting frequency appeared to be increased by $E_2$-VAL and $E_2$-CDS by 7 and 3 days, respectively, but returned to castrate levels by 2 weeks. Only at 14 days were significant differences observed in the mounting frequency of $E_2$-CDS rats, at which point they were greater than $E_2$-VAL and DMSO treated animals.

FIG. 7 shows the effects of $E_2$-CDS (●), $E_2$-VAL (○) and DMSO (◻) on the intromission frequency from day 0 to day 42. Results were analyzed by ANOVA and Student-Newman-Keuls statistics and differences are denoted as follows: (a) different from DMSO, $p<0.05$; different from $E_2$-VAL, $p<0.05$. Intromission frequency was found to be profoundly affected by $E_2$-CDS from 3 days through 28 days. In $E_2$-CDS rats, there was nearly a four-fold increase over castrate levels by 3 days and this increase continued through 28 days. An increase in intromission frequency was observed in $E_2$-VAL treated rats by 3 days, but intromission frequency returned to control levels by 1 week.

Neither $E_2$-CDS, $E_2$-VAL nor DMSO reinstated penile erectile reflexes after orchidectomy.

The test data summarized above illustrates the long-acting effects on male copulatory behavior exhibited by the compounds of formula (I). This evidence for the re-establishment of copulatory behavior in castrated male rats can be summarized as follows:

Animals treated with a single dose of $E_2$-CDS responded with a decrease in mounting latency and intromission latency by 3 days and this effect persisted for at least 28 days. The mounting latency and intromission latency of rats exposed to $E_2$-VAL were diminished for 3 to 7 days and to a lesser extent than in $E_2$-CDS rats. The intromission frequencies of $E_2$-VAL treated rats were increased only at 1 week while animals treated with the $E_2$-CDS increased the number of intromissions by 300% over castrate levels through 14 days and eight-fold over $E_2$-VAL treated animals through 28 days. Intromission frequencies were restored to pre-castrate levels through 4 weeks in $E_2$-CDS treated rats while those exposed to $E_2$-VAL responded similarly for 7 days. Neither ejaculation latencies nor penile reflexes were restored by either $E_2$-CDS or $E_2$-VAL in 4-week orchidectomized rats.

CONCLUSIONS

From the behavior test results described above, it can be concluded:

1. $E_2$-CDS is more efficacious than $E_2$-VAL in stimulating mounting behavior (percent responding) and the effect is 100% through 5 weeks.

2. $E_2$-CDS increases intromission behavior through 28 days over $E_2$-VAL.

3. Mount latency and intromission latency are reduced by $E_2$-CDS to an extent and for a time greater than $E_2$-VAL. The effect lasted for 28 days.

Both estrogens tested decreased the time for orchidectomized animals to initiate the copulatory behavior of mounting and intromission. Additionally, these drugs increased the percentage of animals which exhibited mounts and intromissions. While this effect was apparent with both estrogens evaluated, $E_2$-CDS was more effective and considerably longer acting than the other 17-substituted ester of estradiol, $E_2$-VAL. It appears, then, that the representative chemical delivery system of formula (I), i.e. $E_2$-CDS, improves masculine sexual behavior by increasing the pursuit of the female by the male (i.e. decreasing mount and intromission latency) and by increasing initiation of copulatory behavior (increasing mounts and intromissions).

These data suggest that $E_2$-CDS is a potent, long-acting stimulant of the proceptive components of masculine sexual behavior. These results are particularly surprising in light of the fact that a similar evaluation of the effects of the testosterone-CDS described in Bodor U.S. Pat. No. 4,479,932, i.e. 17β-[(1,4-dihydro-1-methyl-3-pyridinylcarbonyl)oxy]androst-4-en-3-one, in our laboratories failed to show any stimulation of masculine sexual behavior (testosterone-CDS administered in dimethylsulfoxide at a dosage level of 11.9 mg/kg, equivalent to 10 mg/kg of testosterone propionate, with observations made at 0, 3 and 7 days).

Compositions for use in the method of this invention comprise an amount of a compound of formula (I) above or a non-toxic pharmaceutically acceptable salt thereof sufficient to improve male sexual dysfunction, and a non-toxic pharmaceutically acceptable carrier therefor.

Suitable non-toxic pharmaceutically acceptable carriers for use with the selected compound of formula (I), e.g. those less toxic than the target drug species themselves, will be apparent to those skilled in the art of pharmaceutical formulation. See, for example, Remington's Pharmaceutical Sciences, seventeenth edition, ed. Alfonso R. Gennaro, Mack Publishing Company, Easton, Pa. (1985). Obviously, the choice of suitable carriers will depend upon the exact nature of the particular dosage form selected, as well as upon the identity of the compound to be administered. The therapeutic dosage range for administration of a compound of formula (I) for use in treating male sexual dysfunction can be estimated on the basis of animal test results detailed hereinabove. Naturally, such therapeutic dosage ranges will vary with the particular compound of formula (I) used, the size, species and condition of the subject, the severity of the subject's dysfunction, the particular dosage form employed, the route of administration and the like. And the quantity of given dosage form needed to deliver the desired dose will of course depend upon the concentration of the compound of formula (I) in any given pharmaceutical composition/dosage form thereof.

It is contemplated that parenteral dosage forms containing a compound of formula (I), e.g. those formulated for intravenous injection, will be particularly useful in non-human patients. In humans, a dosage form suitable for oral, sublingual, buccal or nasal administration may be preferred. Nevertheless, because of the extremely long-acting effects of a single injection of a compound of formula (I), parenteral administration to human patients would not be impractical.

The compounds of formula (I) exhibit prolonged activity. However, to further sustain action, the active ingredient may be formulated into a sustained release carrier system and/or a route of administration may be selected to slowly release the chemical, e.g. subcutaneous implantation.

It is contemplated that compounds of formula (I) can be used alone to treat sexual dysfunction in cases of psychological impotence which are not complicated by deficits in peripheral androgen-responsive tissues. However, when psychological impotence is associated with peripheral sex organ deficiencies, the use of compounds of formula (I) in combination with androgens (e.g. testosterone, dihydrotestosterone or the like) may be indicated.

While the invention has been described in terms of various preferred embodiments, the skilled artisan will appreciate that various modifications, substitutions, omissions and changes may be made without departing froom the spirit thereof. Accordingly, it is intended that the scope of the present invention be limited solely by the scope of the following claims.

What we claim is:

1. A method for treating male sexual dysfunction, said method comprising administering to a male mammal in need of such treatment, an amount effective to treat said dysfunction in said male mammal of a compound of the formula

[E—DHC]     (I)

or a non-toxic pharmaceutically acceptable salt thereof, wherein [E] is an estrogen and [DHC] is the reduced, biooxidizable, blood-brain barrier-penetrating, lipoidal form of a dihydropyridine⇌pyridinium salt redox carrier.

2. A method according to claim 1, said method comprising administering to a male mammal in need of such treatment, an amount effective to treat said dysfunction in said male mammal of a compound of the formula E-[-DHC]$_n$     (Ia)

or a non-toxic pharmaceuticaly acceptable salt thereof, wherein E— is the residue of an estrogen containing at least one reactive hydroxyl functional group, said residue being characterized by the absence of a hydrogen atom from at least one of said reactive functional groups in said estrogen; n is a positive integer equal to the number of said functional groups from which a hydrogen atom is absent; and [DHC] is the reduced, biooxidizable, blood-brain barrier-penetrating, lipoidal form of a dihydropyridine⇌pyridinium salt redox carrier.

3. A method according to claim 2, wherein n is 1 or 2.

4. A method according to claim 2, wherein E— is the residue of a natural or semisynthetic estrogen.

5. A method according to claim 2, wherein E— is the residue of a 3-monohydroxy, 17-monohydroxy or 3,17-dihydroxy steroid having an aromatic A-ring.

6. A method according to claim 2, wherein E— is a residue of estradiol.

7. A method according to claim 2, wherein E— is the residue of a 3- or 17-monoester of estradiol.

8. A method according to claim 2, wherein E— is the residue of estradiol benzoate, estradiol cypionate, estradiol enanthate, estradiol undecylate, estradiol valerate, estradiol propionate or estradiol undecenylate.

9. A method according to claim 2, wherein E— is the residue of estrone.

10. A method according to claim 2, wherein E— is a residue of estriol.

11. A method according to claim 2, wherein E— is a residue of ethinyl estradiol.

12. A method according to claim 2, wherein E— is the residue of mestranol.

13. A method according to claim 2, wherein E— is the residue of quinestrol, estrazinol or estrofurate or a residue of nylestriol.

14. A method according to claim 2, wherein [DHC] is

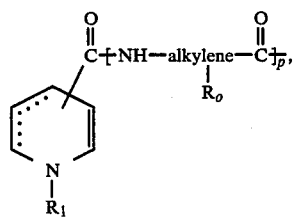

(a')

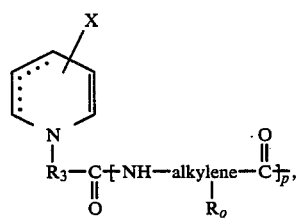

(b')

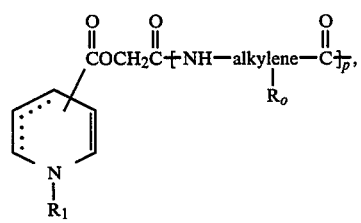

(c')

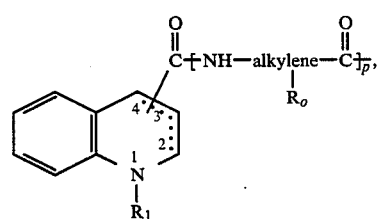

(d')

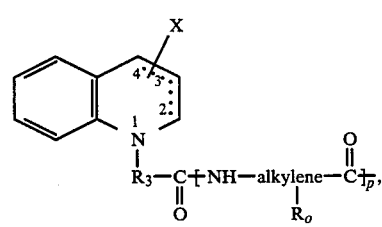

(e')

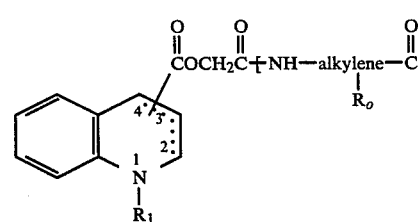

(f')

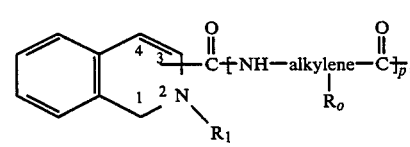

(g')

-continued

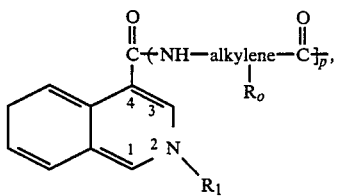
(g')

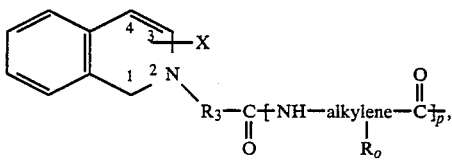
(h')

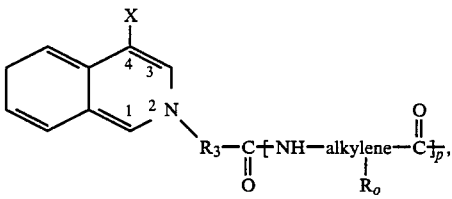
(h'')

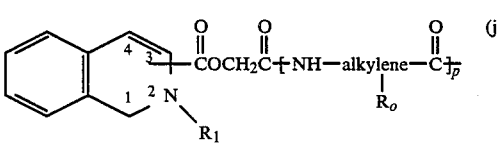
(j')

or

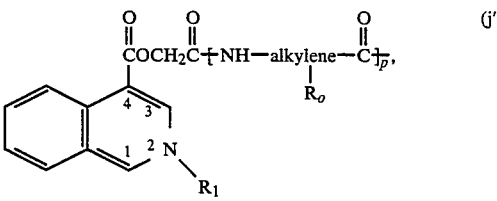
(j'')

wherein the alkylene group can be straight or branched and having 1 to 3 carbon atoms; $R_o$ is a radical identical to the corresponding portion of a natural amino acid; p is 0, 1 or 2, provided that, when p is 2, then the alkylene groups can be the same or different and the $R_o$ radicals can be the same or different; the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R'' wherein R' and R'', which can be the same or different, are each H or $C_1$-$C_7$ alkyl, or X is —CH=NOR''' wherein R''' is H or $C_1$-$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at the 2, 3 or 4 position of the dihydroquinoline ring; and the carbonyl-containing groupings in formulas (g') and (j') and the X substituent in formula (h') can each be attached at the 1, 3 or 4 position of the dihydroisoquinoline ring.

15. A method according to claim 14, wherein p is 0.

16. A method according to claim 14, wherein p is 1.

17. A method according to claim 14, wherein p is 1 or 2, alkylene is —$CH_2$— and $R_o$ is H, —$CH_3$, —$CH(CH_3)_2$, —$CH_2$—$CH(CH_3)_2$,

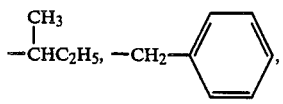

—$(CH_2)_2$—$SCH_3$, —$CH_2$—$CONH_2$ or —$CH_2CH_2$—$CONH_2$.

18. A method according to claim 14, wherein $R_1$ is —$CH_3$.

19. A method according to claim 14, wherein $R_3$ is —$CH_2CH_2$—.

20. A method according to claim 14, wherein X is —$CONH_2$.

21. A method according to claim 14, wherein the depicted carbonyl-containing groupings in formulas (a') and (c') and the X substituent in formula (b') are attached at the 3-position of the dihydropyridine ring; the depicted carbonyl-containing groupings in formulas (d') and (f') and the X substituent in formula (e') are attached at the 3-position of the dihydroquinoline ring; and the depicted carbonyl-containing groupings in formulas (g') and (j') and the X substituent in formula (h') are attached at the 4-position of the dihydroisoquinoline ring.

22. A method according to claim 14, wherein [DHC] is

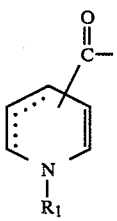

wherein $R_1$ is $C_1$-$C_7$ alkyl, $C_1$-$C_7$ haloalkyl or $C_7$-$C_{10}$ aralkyl, the dotted line indicates the presence of a double bond in either the 4 or 5 position of the dihydropyridine ring and the carbonyl group can be attached at the 2, 3 or 4 position of the dihydropyridine ring.

23. A method according to claim 22, wherein [DHC] is

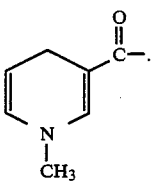

24. A method according to claim 23, wherein E— is a residue of estradiol.

25. A method according to claim 2, wherein the compound of formula (Ia) is 17 β-[(1-methyl-1,4-dihydro-3-pyridinyl)carbonyloxy]estra-1,3,5(10)-trien-3-ol.

* * * * *